United States Patent [19]

Gewirtz et al.

[11] Patent Number: 5,098,890
[45] Date of Patent: Mar. 24, 1992

[54] ANTISENSE OLIGONUCLEOTIDES TO C-MYB PROTO-ONCOGENE AND USES THEREOF

[75] Inventors: Alan M. Gewirtz; Bruno Calabretta, both of Philadelphia, Pa.

[73] Assignee: Temple University-of the Commonwealth System of Higher Education, Philadelphia, Pa.

[21] Appl. No.: 427,659

[22] Filed: Oct. 27, 1989

Related U.S. Application Data

[63] Continuation-in-part of Ser. No. 408,026, Sep. 15, 1989, abandoned, which is a continuation-in-part of Ser. No. 267,901, Nov. 7, 1988, abandoned.

[51] Int. Cl.⁵ .................. A61K 31/70; C07H 21/00
[52] U.S. Cl. .......................... 514/44; 536/27; 536/28; 536/29; 435/6; 935/78
[58] Field of Search ................ 514/44; 536/28, 29

[56] References Cited

U.S. PATENT DOCUMENTS 4,689,320  6/1987  Kaji ............................ 514/44

OTHER PUBLICATIONS

Majello et al., Proc. Natl. Acad. Sci. U.S.A. 83, 9636-9640 (1986).
Westin et al., Proc. Natl. Acad. Sci. U.S.A. 79, 2194 (1982).
Duprey et al., Proc. Natl. Acad. Sci. U.S.A. 82, 6937 (1985).
Clarke et al., Molecular and Cellular Physiology 8, 884-892 (Feb. 1988).
Slamon et al., Science 233, 347 (1986).
Wickstrom et al., Proc. Natl. Acad. Sci. U.S.A. 85, 1028-1032 (Feb. 1988).
Loke et al., Clin. Res. 36(3), 443A (abstract) 1988.
Holt et al., Mol. Cell. Biol. 8, 963-973 (Feb. 1988).
Yakoyama et al., Proc. Natl. Acad. Sci. U.S.A. 84, 7363-7367 (Nov. 1987).
Harel-Bellan et al., J. Immunol. 140, 2431-2435 (Apr. 1988).
Harel-Bellan et al., J. Cell. Biochem. Supplement 12A, 167 (Jan. 1988).
Nishikura et al., Mol. Cell. Biol. 7, 639-649 (Feb. 1987).
Nishikura et al., J. Cell. Biochem. Supplement 11A-D, 146 (1987).
Riabowol et al., Mol. Cell. Biol. 8, 1670-1676 (Apr. 1988).
Mercola et al., Biochem. Biophys. Res. Comm. 147, 288-294 (Aug. 1987).
Groger et al., Proceedings American Assn. for Cancer Research 29, 439 (Mar. 1988).
Shohat et al., Oncogene, 1, 277-283 (1987).
Penno et al., American Journal of Human Genetics 39(3) Supplement, A38 (1986).
Reed et al., J. Cell. Biochem. Supplement 12A, 172 (Jan. 1988).
Weintraub et al., TIG, Jan. 1985, pp. 22-25.
Jaskulski et al., Science 240, 1544-46 (1988).
Paoletti, Anti-Cancer Drug Design 2, 325-331 (1988).
Anfossi et al., Clin. Res. 371, 376A (abstract) (Apr. 1989).
Anfossi et al, Proc. Natl. Acad. Sci. U.S.A. 86, 3379-3383 (May 1989).
Gewirtz et al., Science 245, 180-183 (Jul. 14, 1989).
Caracciolo et al., Science 245, 1107-1110 (Sep. 8, 1989).
Daouk et al., J. Biol. Chem., 263(6), 2442-2446 (1988).
Mariman et al., Genomics, 1, 126-137 (1987).

*Primary Examiner*—Johnnie R. Brown
*Assistant Examiner*—L. Eric Crane
*Attorney, Agent, or Firm*—Seidel, Gonda, Lavorgna & Monaco

[57] ABSTRACT

Oligonucleotides are provided having a nucleotide sequence complementary to at least a portion of the mRNA transcript of the human c-myb gene. These "antisense" oligonucleotides are hybridizable to the c-myb mRNA transcript. Such oligonucleotides are useful in treating hematologic neoplasms and in inducing immunosuppression. They are particularly useful as bone marrow purging agents.

44 Claims, 11 Drawing Sheets

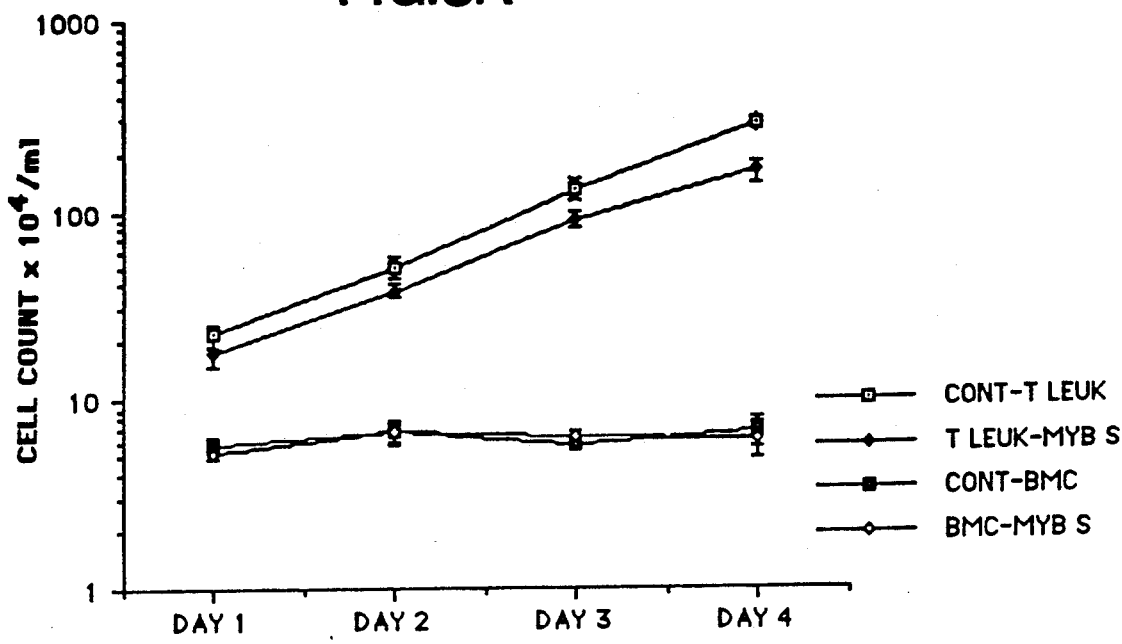
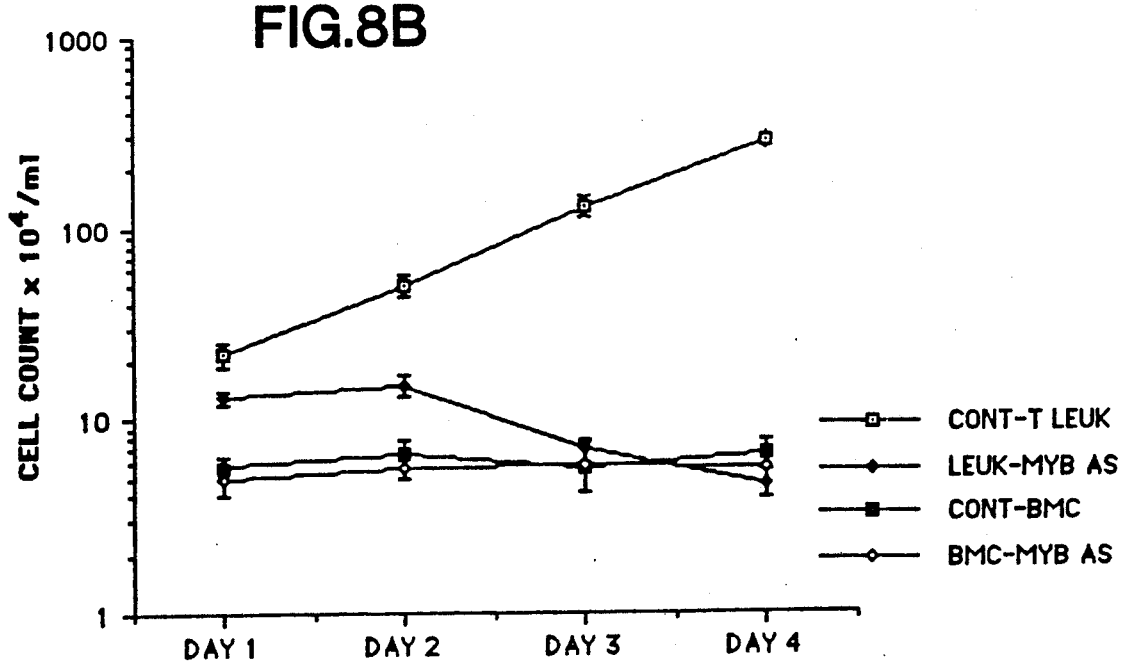

FIG. 10A
FIG. 10B
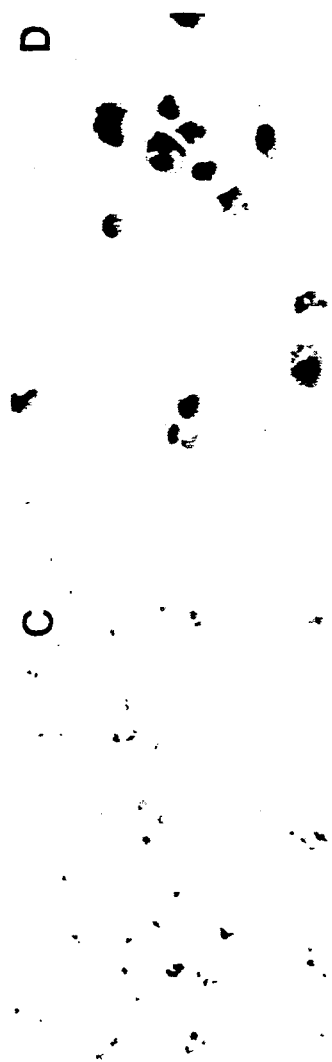
FIG. 10C
FIG. 10D

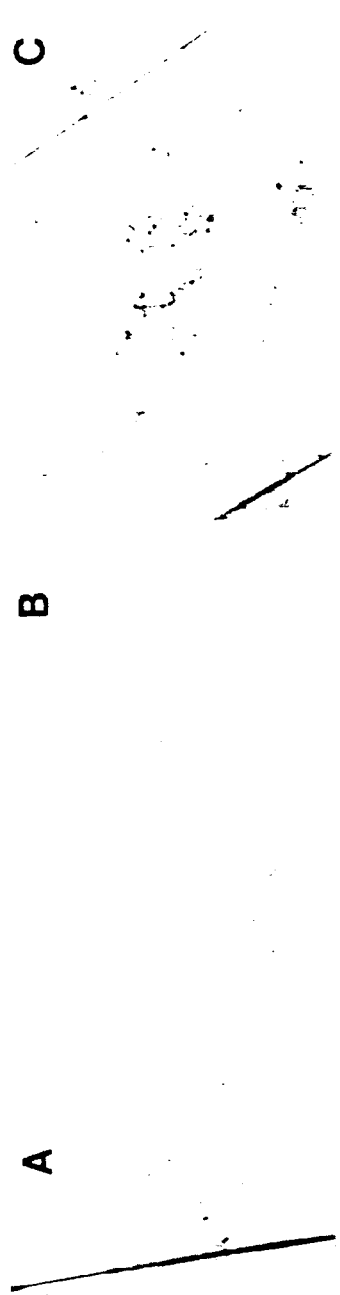
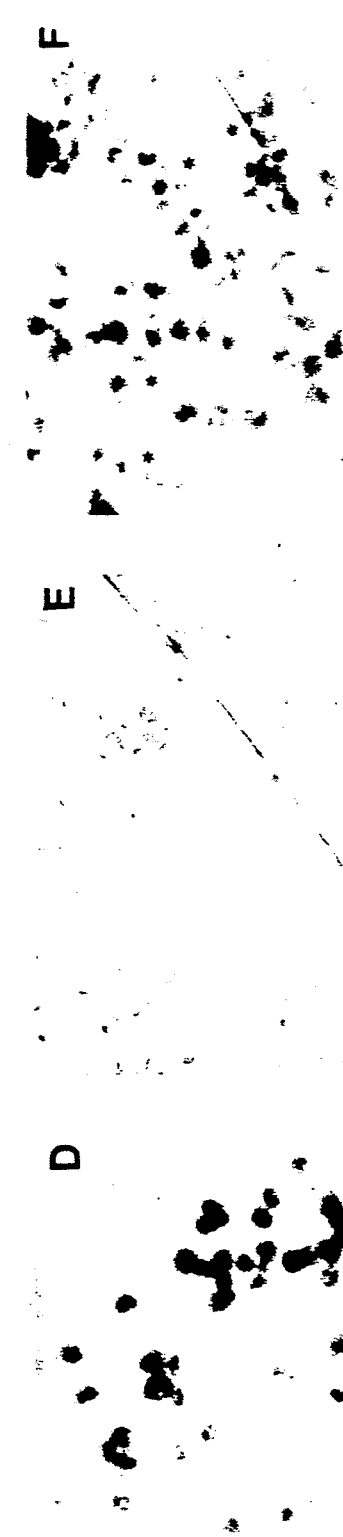
FIG.11A FIG.11B FIG.11C FIG.11D FIG.11E FIG.11F

ANTISENSE OLIGONUCLEOTIDES TO C-MYB PROTO-ONCOGENE AND USES THEREOF

REFERENCE TO GOVERNMENT GRANT

The invention described herein was supported in part by National Institutes of Health grants CA36896, CA01324 and CA46782.

CROSS-REFERENCE TO RELATED APPLICATIONS

This is a continuation-in-part of our co-pending application Ser. No. 408,026, filed Sept. 15, 1989, now abandoned, which is a continuation-in-part of our co-pending application Ser. No. 267,901, filed Nov. 7, 1988.

FIELD OF THE INVENTION

The invention relates to antisense oligonucleotides to proto-oncogenes, and in particular to antisense oligonucleotides to the c-myb gene, and the use of such oligonucleotides as antineoplastic and immunosuppressive agents.

BACKGROUND OF THE INVENTION

Antisense Oligonucleotides

The proto-oncogene c-myb is the normal cellular homologue of the avian myeloblastosis virus-transforming gene v-myb. The c-myb gene codes for a nuclear protein expressed primarily in hematopoietic cells. It is a proto-oncogene, that is, it codes for a protein which is required for the survival of normal, non-tumor cells. When the gene is altered in the appropriate manner, it has the potential to become an oncogene. Oncogenes are genes whose expression within a cell provides some function in the transformation from normal to tumor cell.

The human c-myb gene has been isolated, cloned, and sequenced. Majello et al, Proc. Natl. Acad. Sci. U.S.A. 83, 9636-9640 (1986).

C-myb is preferentially expressed in primitive hematopoietic tissues and hematopoietic tumor cell lines of several species. Westin et al., Proc. Natl. Acad. Sci. U.S.A. 79 2194 (1982). As cells mature, c-myb expression declines. Duprey et al., Proc. Natl. Acad. Sci. U.S.A. 82, 6937, (1985). The constitutive expression of exogenously introduced c-myb inhibits the erythroid differentiation of a murine erythroleukemia cell line (MEL) in response to known inducing agents. Clarke et al., Mol. Cell. Biol. 8, 884-892 (Feb. 1988). Although these data may implicate the c-myb gene product as a potentially important regulator of hematopoietic cell development, this evidence is largely of an indirect nature.

Some investigators report that c-myb may play an important role in regulating hematopoietic cell proliferation, and perhaps differentiation, Slamon et al, Science 233, 347 (1986); Westin et al, supra; Duprey et al, supra. The function of the c-myb proto-oncogene in normal hematopoiesis remains speculative.

Expression of specific genes may be suppressed by oligonucleotides having a nucleotide sequence complementary to the mRNA transcript of the target gene. This "antisense" methodology finds utility as a molecular tool for genetic analysis. Antisense oligonucleotides have been extensively used to inhibit gene expression in normal and abnormal cells in studies of the function of various proto-oncogenes.

Proliferation of the human promyelocytic leukemia cell line HL-60, which over-expresses the c-myc proto-oncogene, is inhibited in a sequence-specific, dose-dependent manner by an antisense oligodeoxynucleotide directed against a predicted hairpin loop containing the initiation codon of human c-myc. Wickstrom et al, Proc. Natl. Acad. Sci. USA 85, 1028-1032 (Feb. 1988). Inhibition of c-myc expression and/or cell proliferation in HL-60 or other cells by c-myc antisense oligonucleotides is described by the following: Loke et al, Clin. Res. 36 (3), 443A (abstract) (1988); Holt et al, Mol. Cell. Biol. 8, 963-973 (Feb. 1988); Yakoyama et al, Proc. Natl. Acad. Sci. U.S.A. 84, 7363-7367 (Nov. 1987); Harel-Bellan et al, J. Immunol. 140, 2431-2435 (Apr. 1988) and J. Cell. Biochem. Supplement 12A, 167 (Jan. 1988).

Antisense methodology has been used to study the expression of c fos, another proto-oncogene. C fos expression and cell transition from $G_0$ to renewed growth is inhibited in 3T3 fibroblast cells transformed with an antisense oligodeoxynucleotide to the proto-oncogene. Nishikura et al, Mol. Cell. Biol. 7, 639-649 (Feb. 1987) and J. Cell. Biochem. Supplement 11A-D, 146 (1987). Also see Riabowol et al, Mol. Cell. Biol. 8, 1670-1676 (April 1988).

Mercola et al, Biochem. Biophys. Res. Comm. 147, 288-294 (Aug. 1987) disclose transfection of v-sis transformed cells with a plasmid directing expression of antisense c-fos RNA. The transfected cells exhibited a decrease in growth.

Groger et al., Proceedings American Assn. for Cancer Research 29, 439 (March 1988) report inhibition of c fos expression in both transformed and non-transformed human hematopoietic cells by an Epstein Barr virus episomal vector containing c-fos antisense RNA.

Transfection of transformed MethA fibroblast and non-transformed 3T3 cells by antisense RNA to the oncogene p53 has resulted in reduction of growth rate and cell proliferation. Shohat et al., Oncogene 1, 277-283 (1987).

Penno et al., American Journal of Human Genetics 39 (3), Supplement, A38 (1986) report inhibition of Y1 mouse adrenal carcinoma cell growth after transfection with a plasmid directing antisense to the Ki-ras oncogene.

Reed et al., J. Cell. Biochem. Supplement 12A, 172, (Jan. 1988) report inhibition of leukemic B cells and normal peripheral blood lymphocytes with antisense oligonucleotides to bcl-2, a gene suggested to have oncogenic potential.

U.S. Pat. No. 4,689,320 discloses inhibition of viruses using antisense oligodeoxynucleotides as anti-viral agents.

While the antisense methodology is a useful tool for genetic analysis, TIG, Jan. 1985, p.22-25, antisense oligonucleotides have not been used as anti-tumor agents in practical applications. Moreover, there have been no reports of antineoplastic agents utilizing antisense oligonucleotides complementary to c-myb mRNA.

Bone Marrow Purging

Bone marrow transplantation is of two types. Allogeneic transplantation comprises the removal of healthy bone marrow cells from a donor and transplantation into a recipient having incomplete, incompetent or diseased bone-marrow. Autologous transplantation involves removal of diseased bone marrow, in vitro purging of the removed marrow of diseased cells, and return of the marrow to the same individual. Autologous transplant is preferable to allogeneic transplant since the need for tissue-typing and immunosuppression of the recipient, and possible tissue rejection, is obviated.

Bone marrow purging of tumor cells in autologous grafting is presently accomplished by in vitro incubation of the transplanted marrow with anti-cancer agents. Many drugs and antibodies have been evaluated as purging agents. See Dicke et al., (eds) Autologous Bone Marrow Transplantation, Proceedings of the Third International Symposium (The University of Texas, M. D. Anderson Hospital and Tumor Institute, Houston, Tex., 1987). Such drugs are highly toxic, and must be used at relatively high doses in order to maximize tumor cell kill. High doses may lead to the death of a substantial number of normal marrow cells and/or graft failure. At lower doses, some tumor cells may survive the purging procedure, accounting for the relatively high rate of malignancy relapse in patients undergoing autologous transplantation.

What is needed is an antineoplastic agent useful for treating hematologic neoplasia. In particular, a bone marrow purging agent is needed which effectively purges marrow of all malignant cells, while leaving normal marrow cells substantially intact.

SUMMARY OF THE INVENTION

Antisense oligonucleotides and pharmaceutical compositions thereof with pharmaceutical carriers are provided. Each oligonucleotide has a nucleotide sequence complementary to at least a portion of the mRNA transcript of the human c-myb gene. The oligonucleotide is hybridizable to the mRNA transcript. Preferably, the oligonucleotide is at least a 15-mer oligodeoxynucleotide, that is, an oligomer containing at least 15 deoxynucleotide residues. Most preferably, the oligodeoxynucleotide is a 15- to 21-mer. While in principle oligonucleotides having a sequence complementary to any region of the c-myb gene find utility in the present invention, oligodeoxynucleotides complementary to a portion of the c-myb mRNA transcript (i) including the translation initiation codon, and/or (ii) beginning with the second codon from the 5' end of the transcript, are particularly preferred.

As used in the herein specification and appended claims, unless otherwise indicated, the term "oligonucleotide" includes both oligomers of ribonucleotide i.e., oligoribonucleotides, and oligomers of deoxyribonucleotide i.e., oligodeoxyribonucleotides (also referred to herein as "oligodeoxynucleotides").

As used herein, unless otherwise indicated, the term "oligonucleotide" also includes oligomers which may be large enough to be termed "polynucleotides".

The terms "oligonucleotide" and "oligodeoxynucleotide" include not only oligomers and polymers of the biologically significant nucleotides, i.e. nucleotides of adenine ("A"), deoxyadenine ("dA"), guanine ("G"), deoxyguanine ("dG"), cytosine ("C"), deoxycytosine ("dC"), thymine ("T") and uracil ("U"), but also oligomers and polymers hybridizable to the c-myb mRNA transcript which may contain other nucleotides. Likewise, the terms "oligonucleotide" and "oligodeoxynucleotide" include oligomers and polymers wherein one or more purine or pyrimidine moieties, sugar moieties or internucleotide linkages is chemically modified.

The term "downstream" when used in reference to a direction along a nucleotide sequence means the 5'→3' direction. Similarly, the term "upstream" means the 3'→5' direction.

The invention provides a method for treating hematologic neoplasms in vivo or ex vivo comprising administering to an individual or cells harvested from the individual an effective amount of c-myb antisense oligonucleotide. The invention also provides a method for treating an individual to induce immunosuppression by administering to the individual an effective amount of such oligonucleotide.

In one embodiment, the method for treating hematologic neoplasms comprises a method for purging bone marrow of such neoplasms. Aspirated bone marrow cells are treated with an effective amount of a c-myb antisense oligonucleotide as described above.

DESCRIPTION OF THE FIGURES

FIG. 8A shows the effect of maintaining a human T cell leukemia line and normal bone marrow mononuclear cells in the absence of c-myb oligodeoxynucleotides (CONT-T LEUK and CONT-BMC, respectively), or in the presence of 40 μg/ml (t=0), followed by 10 μg/ml (t=18 hours), c-myb sense oligodeoxynucleotide (T-LEUK-MYB S and BMC-MYB S, respectively). FIG. 8B shows the effect on the same cell lines of 20 μg/ml (t=0), followed by 5 μg/ml (t=18 hours) of c-myb antisense oligodeoxynucleotide (LEUK-MYB AS, BMC-MYB AS). Daily cell counts and viability determinations were performed. Results presented are the mean ± standard deviation of four experiments. The sense and antisense oligodeoxynucleotides were the same as in FIG. 5.

FIG. 9 is a series of photomicrographs (100×) of T leukemia cells maintained in liquid suspension culture for four days and then cultured in methylcellulose for an additional ten days. Colonies formed by cells in a control culture containing no oligomers appear in FIG. 9A. Colonies formed by cells exposed to c-myb sense oligodeoxynucleotide (20 μg/ml, t=0; plus 5 μg/ml, t=18 hours) are shown in FIG. 9B. Cells exposed to c-myb antisense oligodeoxynucleotide (20 μg/ml, t=0; plus 5 μg/ml, t=18 hours) are shown in FIG. 9C. The sense and antisense oligodeoxynucleotides were the same as in FIG. 5.

FIG. 10 is a series of low and high magnification photomicrographs of Wright's stained cytocentrifuge preparations of T leukemia cells (FIG. 10A: 100×; FIG. 10B: 400×) and a mixture of bone marrow cells and T leukemia cells (FIG. 10C: 100×; FIG. 10D: 400×). T leukemia cells were cultured in the presence of c-myb sense oligodeoxynucleotide. The bone marrow/T-leukemia cell mixture was cultured in the presence of c-myb antisense oligodeoxynucleotide. The sense and antisense oligodeoxynucleotides were the same as in FIG. 5.

FIG. 11 is a series of low and high magnification photomicrographs of myeloid leukemia cells (FIG. 11A: 100×; FIG. 11B: 400×), normal bone marrow cells (FIG. 11C: 100×; FIG. 11D: 400×), and a 1:1 mixture of leukemia cells and normal bone marrow cells (FIG. 11E: 100×; FIG. 11F: 400×) cloned in plasma clot culture after exposure to c-myb antisense oligodeoxynucleotide, and then stained in situ. Stars in FIG. 11F mark mature myeloid elements (polymorphonuclear leukocytes, bands, and metamyelocytes). The antisense oligodeoxynucleotide was the same as in FIG. 5.

DETAILED DESCRIPTION OF THE INVENTION

Figure 1:
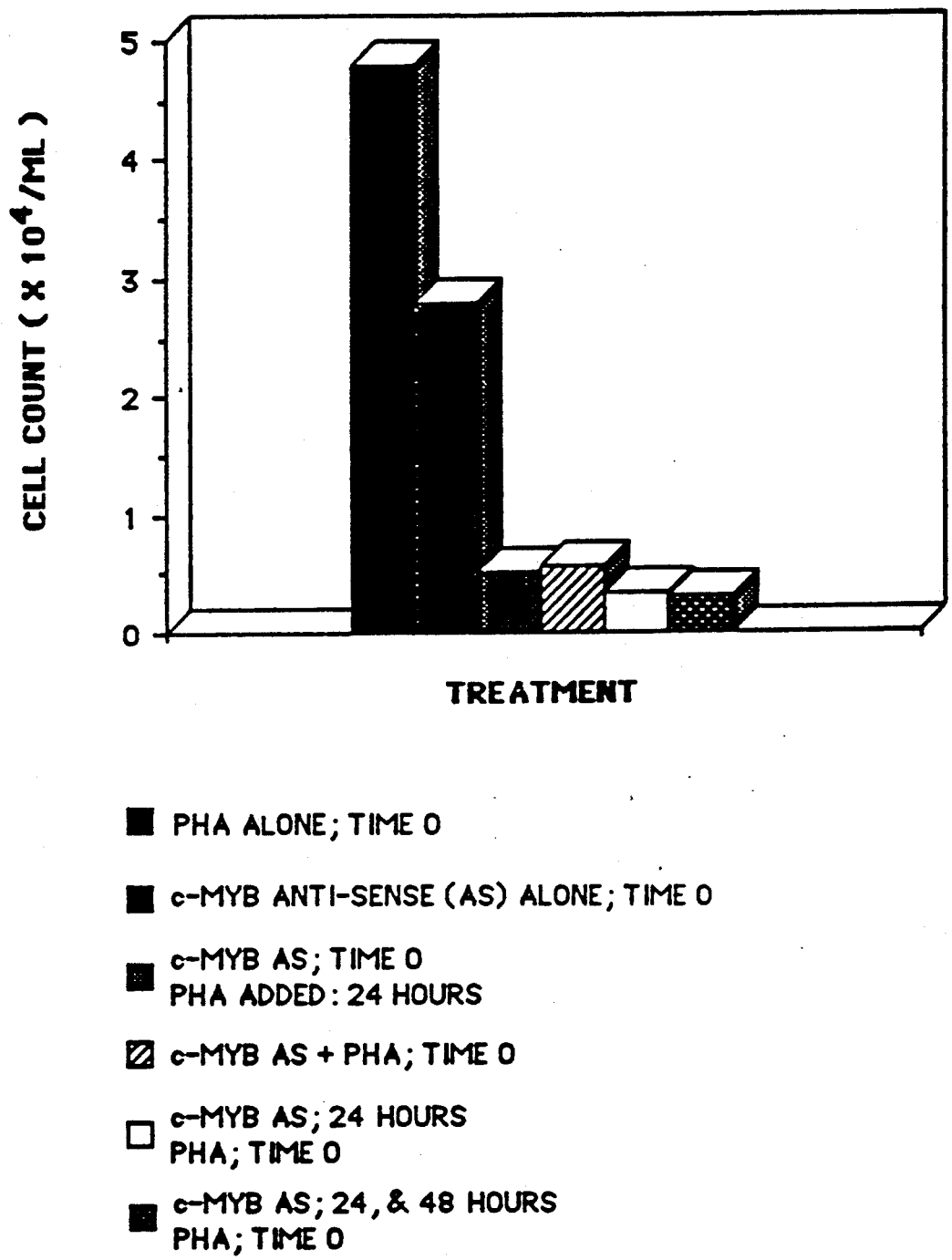
FIG. 1 shows the effect of the c-myb antisense oligodeoxynucleotide in inhibiting phytohemagglutinin-stimulated lymphocyte proliferation. Normal blood lymphocytes were treated at various times with phytohemagglutinin and/or the c-myb antisense oligodeoxynucleotide 5'-GCC CGA AGA CCC CGG CAC-3'.

We have discovered that the c-myb gene plays a critical role in regulating normal human hematopoiesis. We have further discovered a differential sensitivity of normal and malignant hematopoietic cells to c-myb antisense oligonucleotides, that is, oligonucleotides complementary to and hybridizable with the mRNA transcript of the human c-myb gene. This differential sensitivity makes possible the use of c-myb antisense oligonucleotides as effective anti-neoplastic agents, in particular, in the purging of neoplastic cells from bone marrow.

While many drugs and antibodies have been evaluated as bone marrow purging agents, the present invention is particularly advantageous for this application. The c-myb antisense oligonucleotides are much less toxic to normal cells at effective purging doses than known purging agents. A greatly increased engraftment rate of purged marrow is thus possible. Moreover, because of their high therapeutic index, the antisense oligonucleotides of the invention may be employed in combination regimens with more conventional agents, which could then be employed at lower doses.

Since many more normal progenitors survive exposure to the c-myb antisense oligomers than is typically observed after optimal exposure to standard chemotherapeutic agents, higher doses of c-myb antisense may be utilized in comparison to such standard agents.

The c-myl antisense oligonucleotides are also useful as immunosuppressive agents, as they inhibit proliferation of norlal human peripheral blood lymphocytes.

The putative DNA sequence complementary to the mRNA transcript of the human c-myl bene has been reported in Majello et al, Proc. Natl. Acad. Sci. U.S.A. 83, 9636–9640 (1986), the entire disclosure of which is incorporated herein by reference. That sequence, and the predicted 640 amino acid sequence of the putative c-myl protein, are as follows:

GGCGGCAGCGCCCTGCCGACGC
AGCGGGAGGCGGCAGCCCGGT GCTCCCCGCGGCT C

CGGGGAGGGACGCAGGCAGGCGGCGGGCATGGCC
TCGGCGGAGCCCCGCCGCCCGCCGCGCCMet Ala

CGAAGACCCCGGCACAGCATATATAGCAGTGACGAG
Arg Arg Pro Arg His Ser Ile Tyr Ser Ser Asp Glu

GATGATGAGGACTTTGAGATGTGTGACCATGACTAT
Asp Asp Glu Asp Phe Glu Met Cys Asp His Asp Tyr

GATGGGCTGCTTCCCAAGTCTGGAAAGCGTCACTTG
Asp Gly Leu Leu Pro Lys Ser Gly Lys Arg His Leu

GGGAAAACAAGGTGGACCCGGGAAGAGGATGAAAAA
Gly Lys Thr Arg Trp Thr Arg Glu Glu Asp Glu Lys

CTGAAGAAGCTGGTGGAACAGAATGGAACAGATGAC
Leu Lys Lys Leu Val Glu Gln Asn Gly Thr Asp Asp

TGGAAAGTTATTGCCAATTATCTCCCGAATCGAACA
Trp Lys Val Ile Ala Asn Tyr Leu Pro Asn Arg Thr

GATGTGCAGTGCCAGCACCGATGGCAGAAAGTACTA
Asp Val Gln Cys Gln His Arg Trp Gln Lys Val Leu

AACCCTGAGCTCATCAAGGGTCCTTGGACCAAAGAA
Asn Pro Glu Leu Ile Lys Gly Pro Trp Thr Lys Glu

GAAGATCAGAGAGTGATAGAGCTTGTACAGAAATAC
Glu Asp Gln Arg Val Ile Glu Leu Val Gln Lys Tyr

GGTCCGAAACGTTGGTCTGTTATTGCCAAGCACTTA
Gly Pro Lys Arg Trp Ser Val Ile Ala Lys His Leu

AAGGGGAGAATTGGAAAACAATGTAGGGAGAGGTGG
Lys Gly Arg Ile Gly Lys Gln Cys Arg Glu Arg Trp

CATAACCACTTGAATCCAGAAGTTAAGAAAACCTCC
His Asn His Leu Asn Pro Glu Val Lys Lys Thr Ser

TGGACAGAAGAGGAAGACAGAATTATTTACCAGGCA
Trp Thr Glu Glu Glu Asp Arg Ile Ile Tyr Gln Ala

CACAAGAGACTGGGGAACAGATGGGCAGAAATCGCA
His Lys Arg Leu Gly Asn Arg Trp Ala Glu Ile Ala

AAGCTACTGCCTGGACGAACTGATAATGCTATCAAG
Lys Leu Leu Pro Gly Arg Thr Asp Asn Ala Ile Lys

AACCACTGGAATTCTACAATGCGTCGGAAGGTCGAA
Asn His Trp Asn Ser Thr Met Arg Arg Lys Val Glu

CAGGAAGGTTATCTGCAGGAGTCTTCAAAAGCCAGC
Gln Glu Gly Tyr Leu Gln Glu Ser Ser Lys Ala Ser

CAGCCAGCAGTGGCCACAAGCTTCCAGAAGAACAGT
Gln Pro Ala Val Ala Thr Ser Phe Gln Lys Asn Ser

-continued

CATTTGATGGGTTTTGCTCAGGCTCCGCCTACAGCT
His Leu Met Gly Phe Ala Gln Ala Pro Thr Ala

CAACTCCCTGCCACTGGCCAGCCCACTGTTAACAAC
Gln Leu Pro Ala Thr Gly Gln Pro Thr Val Asn Asn

GACTATTCCTATTACCACATTTCTGAAGCACAAAAT
Asp Tyr Ser Tyr Tyr His Ile Ser Glu Ala Gln Asn

GTCTCCAGTCATGTTCCATACCCTGTAGCGTTACAT
Val Ser Ser His Val Pro Tyr Pro Val Ala Leu His

GTAAATATAGTCAATGTCCCTCAGCCAGCTGCCGCA
Val Asn Ile Val Asn Val Pro Gln Pro Ala Ala Ala

GCCATTCAGAGACACTATAATGATGAAGACCCTGAG
Ala Ile Gln Arg His Tyr Asn Asp Glu Asp Pro Glu

AAGGAAAAGCGAATAAAGGAATTAGAATTGCTCCTA
Lys Glu Lys Arg Ile Lys Glu Leu Glu Leu Leu Leu

ATGTCAACCGAGAATGAGCTAAAAGGACAGCAGGTG
Met Ser Thr Glu Asn Glu Leu Lys Gly Gln Gln Val

CTACCAACACAGAACCACACATGCAGCTACCCCGGG
Leu Pro Thr Gln Asn His Thr Cys Ser Tyr Pro Gly

TGGCACAGCACCACCATTGCCGACCACACCAGACCT
Trp His Ser Thr Thr Ile Ala Asp His Thr Arg Pro

CATGGAGACAGTGCACCTGTTTCCTGTTTGGGAGAA
His Gly Asp Ser Ala Pro Val Ser Cys Leu Gly Glu

CACCACTCCACTCCATCTCTGCCAGCGGATCCTGGC
His His Ser Thr Pro Ser Leu Pro Ala Asp Pro Gly

TCCCTACCTGAAGAAAGCGCCTCGCCAGCAAGGTGC
Ser Leu Pro Glu Glu Ser Ala Ser Pro Ala Arg Cys

ATGATCGTCCACCAGGGCACCATTCTGGATAATGTT
Met Ile Val His Gln Gly Thr Ile Leu Asp Asn Val

AAGAACCTCTTAGAATTTGCAGAAACACTCCAATTT
Lys Asn Leu Leu Glu Phe Ala Glu Thr Leu Gln Phe

ATAGATTCTTTCTTAAACACTTCCAGTAACCATGAA
Ile Asp Ser Phe Leu Asn Thr Ser Ser Asn His Glu

AACTCAGACTTGGAAATGCCTTCTTTAACTTCCACC
Asn Ser Asp Leu Glu Met Pro Ser Leu Thr Ser Thr

CCCCTCATTGGTCACAAATTGACTGTTACAACACCA
Pro Leu Ile Gly His Lys Leu Thr Val Thr Thr Pro

TTTCATAGAGACCAGACTGTGAAAACTCAAAAGGAA
Phe His Arg Asp Gln Thr Val Lys Thr Gln Lys Glu

AATACTGTTTTTAGAACCCCAGCTATCAAAAGGTCA
Asn Thr Val Phe Arg Thr Pro Ala Ile Lys Arg Ser

ATCTTAGAAAGCTCTCCAAGAACTCCTACACCATTC
Ile Leu Glu Ser Ser Pro Arg Thr Pro Thr Pro Phe

AAACATGCACTTGCAGCTCAAGAAATTAAATACGGT
Lys His Ala Leu Ala Ala Gln Glu Ile Lys Tyr Gly

CCCCTGAAGATGCTACCTCAGACACCCTCTCATCTA
Pro Leu Lys Met Leu Pro Gln Thr Pro Ser His Leu

GTAGAAGATCTGCAGGATGTGATCAAACAGGAATCT
Val Glu Asp Leu Gln Asp Val Ile Lys Gln Glu Ser

GATGAATCTGGATTTGTTGCTGAGTTTCAAGAAAAT
Asp Glu Ser Gly Phe Val Ala Glu Phe Gln Glu Asn

GGACCACCCTTACTGAAGAAAATCAAACAAGAGGTG
Gly Pro Pro Leu Leu Lys Lys Ile Lys Gln Glu Val

GAATCTCCAACTGATAAATCAGGAAACTTCTTCTGC
Glu Ser Pro Thr Asp Lys Ser Gly Asn Phe Phe Cys

TCACACCACTGGGAAGGGGACAGTCTGAATACCCAA
Ser His His Trp Glu Gly Asp Ser Leu Asn Thr Gln

CTGTTCACGCAGACCTCGCCTGTGCGAGATGCACCG
Leu Phe Thr Gln Thr Ser Pro Val Arg Asp Ala Pro

AATATTCTTACAAGCTCCGTTTTAATGGCACCAGCA
Asn Ile Leu Thr Ser Ser Val Leu Met Ala Pro Ala

TCAGAAGATGAAGACAATGTTCTCAAAGCATTTACA
Ser Glu Asp Glu Asp Asn Val Leu Lys Ala Phe Thr

GTACCTAAAAACAGGTCCCTGGCGAGCCCCTTGCAG
Val Pro Lys Asn Arg Ser Leu Ala Ser Pro Leu Gln

CCTTGTAGCAGTACCTGGGAACCTGCATCCTGTGGA
Pro Cys Ser Ser Thr Trp Glu Pro Ala Ser Cys Gly

AAGATGGAGGAGCAGATGACATCTTCCAGTCAAGCT
Lys Met Glu Glu Gln Met Thr Ser Ser Gln Ala

CGTAAATACGTGAATGCATTCTCAGCCCGGACGCTG
Arg Lys Tyr Val Asn Ala Phe Ser Ala Arg Thr Leu

GTCATGTGAGACATTTCCAGAAAAGCATTATGGTTTTC
Val Met

AGAACAGTTCAAGTTGACTTGGGATATATCATTCCTCA

ACATGAAACTTTTCATGAATGGGAGAAGAACCTATTT

TTGTTGTGGTACAACAGTTGAGAGCACGACCAAGTGC

ATTTAGTTGAATGAAGTCTTCTTGGATTTCACCCAACT

AAAAGGATTTTTAAAAATAAATAACAGTCTTACCTAAA

TTATTAGGTAATGAATTGTAGCCAGTTGTTAATATCTT

AATGCAGATTTTTTTAAAAAAAAAACATAAAATGATTTA

TCTGGTATTTTAAAGGATCCAACAGATCAGTATTTTTT

CCTGTGATGGGTTTTTTGAAATTTGACACATTAAAAGG

TACTCCAGTATTTCACTTTTCTCGATCACTAAACATAT

GCATATATTTTTAAAAATCAGTAAAAGCATTACTCTAA

GTGTAGACTTAATACCATGTGACATTTAATCCAGATTG

TAAATGCTCATTTATGGTTAATGACATTGAAGGTACAT

TTATTGTACCAAACCATTTTATGAGTTTTCTGTTAGCTT

GCTTTAAAAATTATTACTGTAAGAAATAGTTTTATAAA

AAATTATATTTTTATTCAGTAATTTAATTTTGTAAATGC

CAAATGAAAAACGTTTTTTGCTGCTATGGTCTTAGCCT

GTAGACATGCTGCTAGTATCAGAGGGGCAGTACAGCTT

GGACAGAAAGAAAAGAAACTTGGTGTTAGGTAATTGA

CTATGCACTAGTATTTCAGACTTTTTAATTTTATATATA

TATACATTTTTTTTCCTTCTGCAATACATTTGAAAACTT

GTTTGGCAGACTCTGCATTTTTTATTGTGGTTTTTTTGT

TATTGTTGGTTTATACAAGCATGCGTTGCACTTCTTTTT

TGGGAGATGTGTGTTGTTGATGTTCTATGTTTTGTTTT

GTGTGTAGCCTGACTGTTTTATAATTTGGGAGTTCTCG

ATTTGATCCGCATCCCCTGTGGTTTCTAAGTGTATGGT

CTCAGAACTGTTGCATGGATCCTGTGTTTGCAACTGG

GGAGACAGAAACTGTGGTTGATAGCCAGTCACTGCCT

-continued
TAAGAACATTTGATGCAAGATGGCCAGCACTGAACTT

TTGAGATATGACGGTGTACTTACTGCCTTGTAGCAAA

ATAAAGATGTGCCCTTATTTTAAAAAAAAAAAAAA

The initiation codon ATG appears at position 114, preceded by a 5'-untranslated region. The termination codon TGA at position 2034 is followed by a 3'-untranslated region spanning about 1200 nucleotides, which is followed by a poly(A) tail of about 140 nucleotides.

The antisense oligonucleotides of the invention may be synthesized by any of the known chemical oligonucleotide synthesis methods. Such methods are generally described, for example, in Winnacker, *From Genes to Clones: Introduction to Gene Technology*. VCH Verlagsgesellschaft mbH (H. Ibelgaufts trans. 1987).

Any of the known methods of oligonucleotide synthesis may be utilized in preparing the instant antisense oligonucleotides.

The antisense oligonucleotides are most advantageously prepared by utilizing any of the commercially available, automated nucleic acid synthesizers. The device utilized to prepare the oligonucleotides described herein, the Applied Biosystems 380B DNA Synthesizer, utilizes β-cyanoethyl phosphoramidite chemistry.

Since the complete nucleotide synthesis of DNA complementary to the c-myb mRNA transcript is known, antisense oligonucleotides hybridizable with any portion of the mRNA transcript may be prepared by the oligonucleotide synthesis methods known to those skilled in the art.

While any length oligonucleotide may be utilized in the practice of the invention, sequences shorter than 15 bases may be less specific in hybridizing to the target c-myb mRNA, and may be more easily destroyed by enzymatic digestion. Hence, oligonucleotides having 15 or more nucleotides are preferred. Sequences longer than 18 to 21 nucleotides may be somewhat less effective in inhibiting c-myb translation because of decreased uptake by the target cell. Thus, oligomers of 15-21 nucleotides are most preferred in the practice of the present invention, particularly oligomers of 15-18 nucleotides.

Oligonucleotides complementary to and hybridizable with any portion of the c-myb mRNA transcript are, in principle, effective for inhibiting translation of the transcript, and capable of inducing the effects herein described. It is believed that translation is most effectively inhibited by blocking the mRNA at a site at or near the initiation codon. Thus, oligonucleotides complementary to the 5'-terminal region of the c-myb mRNA transcript are preferred. It is believed that secondary or tertiary structure which might interfere with hybridization is minimal in this region. Moreover, it has been suggested that sequences that are too distant in the 3' direction from the initiation site may be less effective in hybridizing the mRNA transcripts because of a "read-through" phenomenon whereby the ribosome is postulated to unravel the antisense/sense duplex to permit translation of the message. See, e.g. Shakin, J. Biochemistry 261, 16018 (1986).

The antisense oligonucleotide is preferably directed to a site at or near the initiation codon for protein synthesis. Oligonucleotides complementary to a portion of the c-myb mRNA including the initiation codon (the first myb transcript, comprising nucleotides 114-116 of the complete transcript) are preferred, as are oligonucleotides complementary to the portion of the c-myb mRNA beginning with the codon adjacent to the initiation codon (the second codon from the 5' end of the translated portion, comprising nucleotides 117-119 of the complete transcript.

While antisense oligomers complementary to the 5'-terminal region of the c-myb transcript are preferred, particularly the region including the initiation codon, it should be appreciated that useful antisense oligomers are not limited to those complementary to the sequences found in the translated portion (nucleotides 114 to 2031) of the mRNA transcript, but also includes oligomers complementary to nucleotide sequences contained in, or extending into, the 5'- and 3'-untranslated regions. We have shown that oligomers whose complementarity extends into the 5'-untranslated region of the c-myb transcript are particularly effective in inhibiting translation. Oligomers having a nucleotide sequence complementary to a portion of the c-myb mRNA transcript including at least a portion of the 5'-untranslated region therefore comprise one group of preferred oligomers.

The following 15- through 21-mer oligodeoxynucleotides are complementary to the c-myb mRNA transcript beginning with the second codon of the translated portion of transcript (nucleotides 117-119 of the complete transcript):

5'-GCT GTG CCG GGG TCT TCG GGC-3'

5'-CT GTG CCG GGG TCT TCG GGC-3'

5'-T GTG CCG GGG TCT TCG GGC-3'

5'-GTG CCG GGG TCT TCG GGC-3'

5'-TG CCG GGG TCT TCG GGC-3'

5'-G CCG GGG TCT TCG GGC-3'

5'-CCG GGG TCT TCG GGC-3'

Similarly, the following 15- through 21-mer oligodeoxynucleotides are complementary to the c-myb mRNA transcript beginning with nucleotide 111 and extending through the initiation site:

5'-CCG GGG TCT TCG GGC CAT GGC-3'

5'-CG GGG TCT TCG GGC CAT GGC-3'

5'-G GGG TCT TCG GGC CAT GGC-3'

5'-GGG TCT TCG GGC CAT GGC-3'

5'-GG TCT TCG GGC CAT GGC-3'

5'-G TCT TCG GGC CAT GGC-3'

5'-TCT TCG GGC CAT GGC-3'

Oligonucleotides hybridizable to the c-myb mRNA transcript finding utility according to the present invention include not only native oligomers of the biologically significant nucleotides, i.e., A, dA, G, dG, C, dC, T and U, but also oligonucleotide species which have been modified for improved stability and/or lipid solubility. For example, it is known that enhanced lipid solubility and/or resistance to nuclease digestion results by substituting a methyl group or sulfur atom for a phosphate oxygen in the internucleotide phosphodiester linkage. The phosphorothioates, in particular, are stable to nuclease cleavage and soluble in lipid. They may be synthesized by known automatic synthesis methods.

The antisense oligonucleotides of the invention inhibit normal human hematopoiesis. However, they inhibit the growth of malignant hematopoietic cells at a significantly lower concentration than normal cells. This pharmaceutically significant differential sensitivity makes the instant oligonucleotides very useful in treating hematologic neoplasms.

Hematologic neoplastic cells believed sensitive to the instant c-myb antisense oligonucleotides include, for example, myeloid and lymphatic leukemia cells, malignant plasma (myeloma) cells and lymphoma cells. The appearance of these cells in the bone marrow and elsewhere in the body is associated with various disease conditions, such as all of the various French-American-British (FAB) subtypes of acute myeloid and lymphatic leukemia; chronic lymphatic and myeloid leukemia; plasma cell myeloma and plasma cell dyscrasias; the various non-Hodgkin's lymphomas as described, for example, in the Working Formulation classification, Devita, *Cancer: Principles and Practice of Oncology* (2d ed. 1985), p. 1634; and possibly Hodgkin's disease.

Hematologic neoplastic cells would likely arise de novo in the marrow. In Hodgkin's disease, and in some of the various lymphomas, tumor cells may metastasize to the marrow from a primary tumor situated elsewhere in the body.

While inhibition of c-myb mRNA translation is possible utilizing either antisense oligoribonucleotides or oligodeoxyribonucleotides, oligoribonucleotides are more susceptible to enzymatic attack by ribonucleases than deoxyribonucleotides. Hence, oligodeoxyribonucleotides are preferred in the practice of the present invention.

The antisense oligonucleotides of the invention find utility as bone marrow purging agents. They may be utilized in vitro to cleanse bone marrow contaminated by hematologic neoplasms. They are useful as purging agents in either allogeneic or autologous bone marrow transplantation. They are particularly effective in the treatment of hematological malignancies or other neoplasias which metastasize in the bone marrow.

According to a method for bone marrow purging, bone marrow is harvested from a donor by standard operating room procedures from the iliac bones of the donor. Methods of aspirating bone marrow from donors are well known in the art. Examples of apparatus and processes for aspirating bone marrow from donors are disclosed in U.S. Pat. Nos. 4,481,946 and 4,486,188. Sufficient marrow is withdrawn so that the recipient, who is either the donor (autologous transplant) or another individual (allogeneic transplant), may receive from about $4 \times 10^8$ to about $8 \times 10^8$ processed marrow cells per kg of bodyweight. This generally requires aspiration of about 750 to about 1000 ml of marrow. The aspirated marrow is filtered until a single cell suspension, known to those skilled in the art as a "buffy coat" preparation, is obtained. This suspension of leukocytes is treated with c-myb antisense oligonucleotides in a suitable carrier, advantageously in a concentration of about 8 mg/ml. Alternatively, the leucocyte suspension may be stored in liquid nitrogen using standard procedures known to those skilled in the art until purging is carried out. The purged marrow can be stored frozen in liquid nitrogen until ready for use. Methods of freezing bone marrow and biological substances are disclosed, for example, in U.S. Pat. Nos. 4,107,937 and 4,117,881.

Other methods of preparing bone marrow for treatment with c-myb antisense may be utilized, which methods may result in even more purified preparations of hematopoietic cells than the aforesaid buffy coat preparation.

One or more hematopoietic growth factors may be added to the aspirated marrow or buffy coat preparation to stimulate growth of hematopoietic neoplasms, and thereby increase their sensitivity to the toxicity of the c-myb antisense oligonucleotides. Such hematopoietic growth factors include, for example, interleukin-3 and granulocyte macrophage colony stimulating factor (GM-CSF). The recombinant human versions of such growth factors are advantageously employed.

After treatment with the antisense oligonucleotides, the cells to be transferred are washed with autologous plasma or buffer to remove unincorporated oligomer. The washed cells are then infused into the recipient.

The instant c-myb antisense oligonucleotides also inhibit proliferation of human peripheral blood lymphocytes. Accordingly, they are useful as immunosuppressive agents, that is, they may be utilized to inhibit immune response, particularly cellular response. They are particularly useful in situations where rapid, but short term, inactivation of the immune system is desirable. Such circumstances may include, but are not limited to, acute graft-versus-host disease, acute organ rejection (heart, liver, kidney, pancreas), and flares of autoimmune-type diseases such as acute systemic lupus erythematosus, rheumatoid arthritis and multiple sclerosis.

For in vivo use, the antisense oligonucleotides may be combined with a pharmaceutical carrier, such as a suitable liquid vehicle or excipient and an optional auxiliary additive or additives. The liquid vehicles and excipients are conventional and commercially available. Illustrative thereof are distilled water, physiological saline, aqueous solution of dextrose, and the like. For in vivo antineoplastic or immunosuppressive use, the c-myb mRNA antisense oligonucleotides are preferably administered intravenously. It is also possible to administer such compounds ex vivo by isolating lymphocytes from peripheral blood, treating them with the antisense oligonucleotides, then returning the treated lymphocytes to the peripheral blood of the donor. Ex vivo techniques have been utilized in treatment of cancer patients with interleukin-2 activated lymphocytes.

In addition to administration with conventional carriers, the antisense oligonucleotides may be administered by a variety of specialized oligonucleotide delivery techniques. For example, oligonucleotides have been successfully encapsulated in unilameller liposomes. Reconstituted Sendai virus envelopes have been successfully used to deliver RNA and DNA to cells. Arad et al., Biochem. Biophy. Acta. 859, 88–94 (1986).

For ex vivo antineoplastic application, such as, for example, in bone marrow purging, the c-myb antisense oligonucleotides may be administered in amounts effective to kill neoplastic cells while maintaining the viability of normal hematologic cells. Such amounts may vary depending on the nature and extent of the neoplasm, the particular oligonucleotide utilized, the relative sensitivity of the neoplasm to the oligonucleotide, and other factors. Concentrations from about 10 to 100 $\mu$g/ml per $10^5$ cells may be employed, preferably from about 40 to 60 $\mu$g/ml per $10^5$ cells. Supplemental dosing of the same or lesser amounts of oligonucleotide are advantageous to optimize the treatment. Thus, for purging bone marrow containing $2 \times 10^7$ cell per ml of marrow volume, dosages of from about 2 to 20 mg antisense per ml of marrow may be effectively utilized, preferably from about 8 to 12 mg/ml. Greater or lesser amounts of oligonucleotide may be employed.

For in vivo use, the c-myb antisense oligonucleotides may be administered in an amount sufficient to result in extracellular concentrations approximating the above stated in vitro concentrations. The actual dosage administered may take into account the size and weight of the patient, whether the nature of the treatment is prophylactic or therapeutic in nature, the age, weight, health and sex of the patient, the route of administration, and other factors. The daily dosage may range from about 0.1 to 1,000 mg oligonucleotide per day, preferably from about 10 to about 1,000 mg per day. Greater or lesser amounts of oligonucleotide may be administered, as required.

The present invention is described in greater detail in the following non-limiting examples.

EXAMPLE 1

Effect of c-myb Antisense Olioomer on Normal Peripheral Blood Lymphocyte Proliferation in Response to PHA Exposure The c-myb antisense oligonucleotides have immunosuppressant activity, as demonstrated by the following experiment wherein lymphocyte proliferation is markedly suppressed by treatment with the oligomer. Normal blood lymphocytes were treated with the c-myb antisense oligodeoxynucleotide 5'-GTG CCG GGG TCT TCG GGC-3' at a final concentration of 40 $\mu$g/ml. C-myb antisense and/or phytohaemagglutinin (PHA) were added to the cells as follows: (i) PHA alone, t=0 (no oligonucleotide); (ii) c-myb antisense alone, t=0 (no PHA); (iii) c-myb antisense, t=0; PHA, t=24 hours; (iv) c-myb antisense +PHA, both t=0; (v) PHA, t=0; c-myb antisense, t=24 hours; and (vi) PHA, t=0; c-myb antisense t=24 and 48 hours. Cell counts were performed at t=day 6. The results are shown in FIG. 1. As is evident from the figure, PHA treatment alone resulted in marked cell proliferation when compared to cells exposed to 40 $\mu$g/ml c-myb antisense oligomer. One dose of oligomer alone in the absence of PHA did not appear to be toxic to normal lymphocytes through day 6. As can be noted in FIG. 1, however, once cells were exposed to PHA, either simultaneously or within 24 hours of c-myb antisense treatment, the 40 $\mu$g/ml dose became very toxic to the cells, as manifested by the low cell numbers present on day 6. Additional doses of c-myb at 24 and 48 hours did not appear to be essential in order to inhibit PHA-induced proliferation of normal cells.

EXAMPLE 2

Figure 7A:
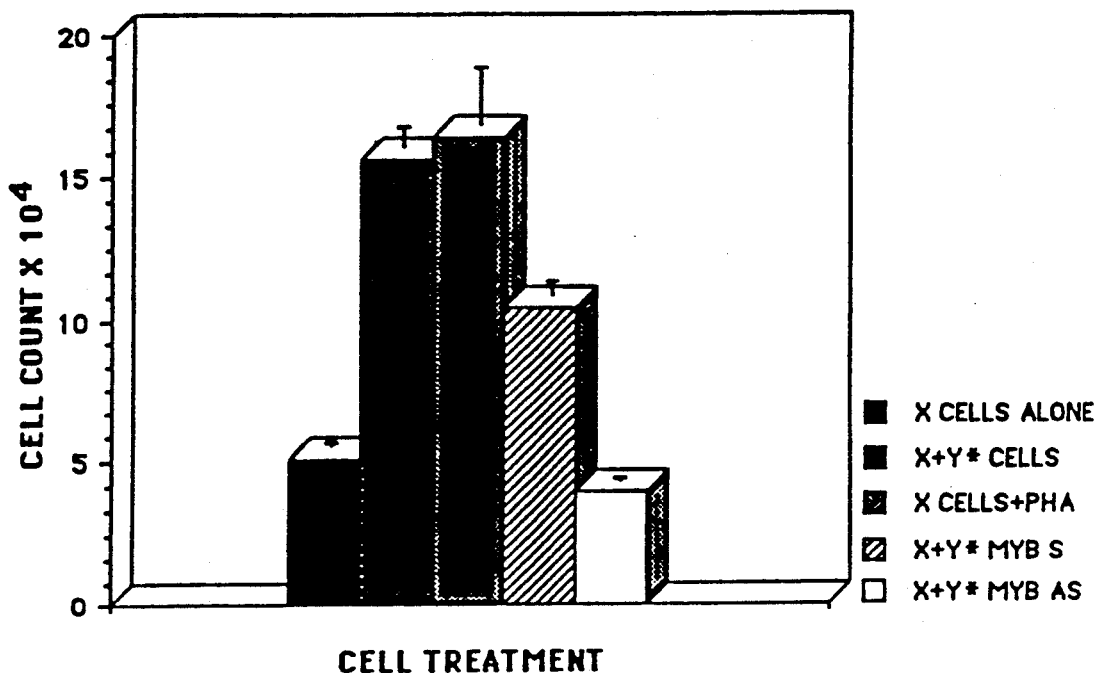
FIG. 7 shows the effect of the same c-myb antisense oligodeoxynucleotide in inhibiting lymphocyte proliferation in a mixed lymphocyte reaction, as determined by cell count (FIG. 7A) and tritiated thymidine incorporation (FIG. 7B).
Figure 7B:
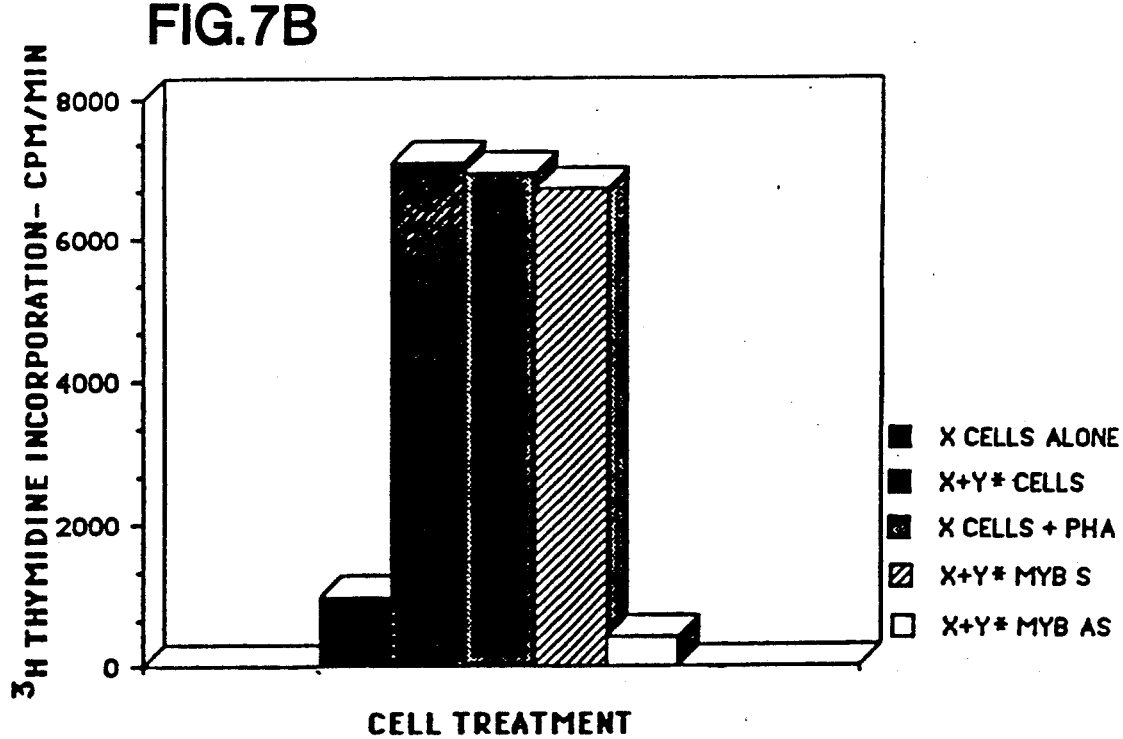

Effect of c-myb Antisense Oligomer on Normal Peripheral Blood Lymphocyte Proliferation in Mixed Lymphocyte Reaction The following experiment further demonstrates the immunosuppressant activity of the c-myb antisense oligonucleotides. Normal peripheral blood mononuclear cells (FIG. 7: X cells) were either stimulated with PHA alone or mixed with mitomycin C-treated mononuclear cells from another normal donor (FIG. 7: Y* cells). In two cultures, X cells were pre-incubated for 18 hours with 40 $\mu$g/ml of the c-myb sense oligonucleotide 5'-GCC CGA AGA CCC CGG CAC-3', or the c-myb antisense oligonucleotide used in Example 1. The thus treated X cells were then mixed with Y* cells. At 24 and 48 hours, an additional 10 $\mu$g/ml of oligomers was added to the cultures. After five days, cell counts were performed (FIG. 7A), and tritiated thymidine incorporation was determined (FIG. 7B). Inhibition of mixed lymphocyte-induced cell proliferation and tritiated thymidine incorporation was observed only with the c-myb antisense-treated cells.

EXAMPLE 3

Differential Sensitivity of Tumor (ARH-77) and Normal Progenitor Cells Toward c-myb Oligonucleotide The following experiment was performed to establish the differential sensitivity of normal progenitor and tumor cells to c-myb antisense oligonucleotide. Accordingly, tumor cells ($1 \times 10^5$ cells/ml) or normal human marrow cells ($1 \times 10^5$ cells/ml) were cultured alone or mixed together in a 1:1 ratio (total cell number cultured = $1 \times 10^5$ cells/ml) in the presence or absence of c-myb oligonucleotides.

Figure 2A:
FIG. 2 is a series of microscopic (200×) photographs of untreated seven-day cultures of normal human myeloid cell colonies (FIG. 2A); ARH-77, an IgG-secreting plasma cell leukemia (FIG. 2B); and HL-60 promyelocytic leukemia cells (FIG. 2C).
Figure 2B:
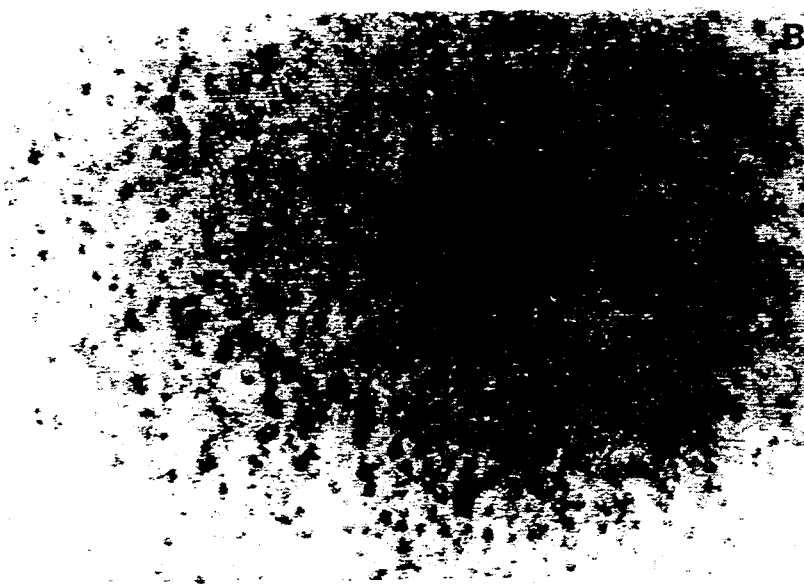
Figure 2C:
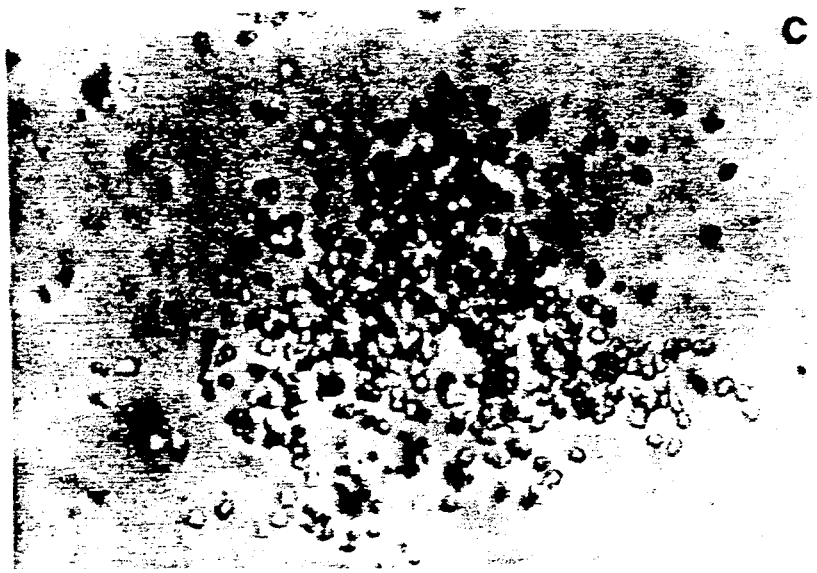

FIGS. 2A, 2B and 2C respectively show a high magnification view (200$\times$) of untreated (A) normal human myeloid cell colonies, (B) ARH-77 cells (IgG-secreting plasma cell leukemia, ATCC No. CRL 1621), and (C) HL-60 (promyelocytic leukemia cells), all after seven days of culture. It can be observed that the normal marrow cells grow in widely separate aggregates of relatively small cell number. The tumor cells grow much more luxuriantly, and appear to overgrow each other.

Figure 3A:
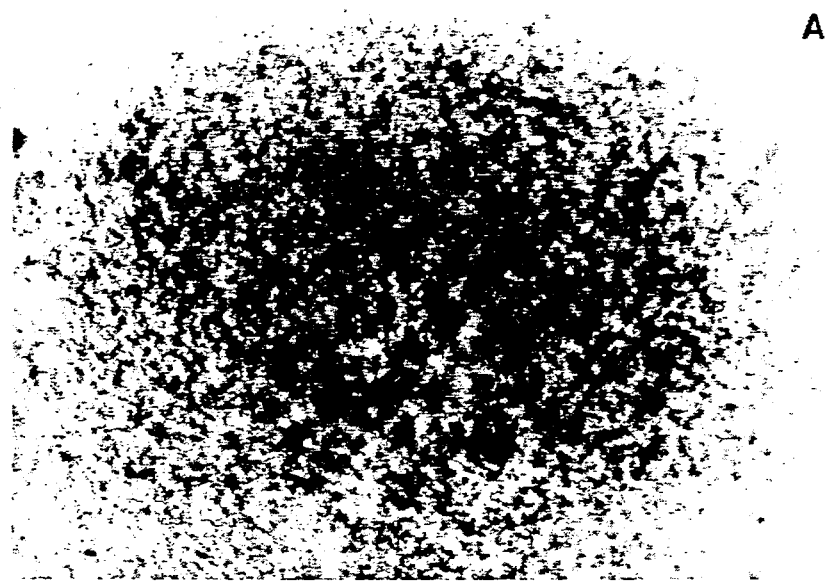
FIG. 3 is a series of microscopic (40×) photographs of a 1:1 mixture of ARH-77 cells and normal hematopoietic progenitor cells exposed to 40 µg/ml (t=0) plus 20 µg/ml (t=18 hours) of the c-myb sense oligodeoxynucleotide 5'-GCC CGA AGA CCC CGG CAC-3' (FIG. 3A); 10 µg/ml (t=0) plus 5 µg/ml (t=18 hours) of the c-myb antisense oligodeoxynucleotide 5'-GTG CCG GGG TCT TCG GGC-3' (FIG. 3B); and 40 µg/ml (t=0) plus 20 µg/ml (t=18 hours) of the same c-myb antisense oligomer (FIG. 3C). The photographs were taken at t=day 7.
Figure 3B:
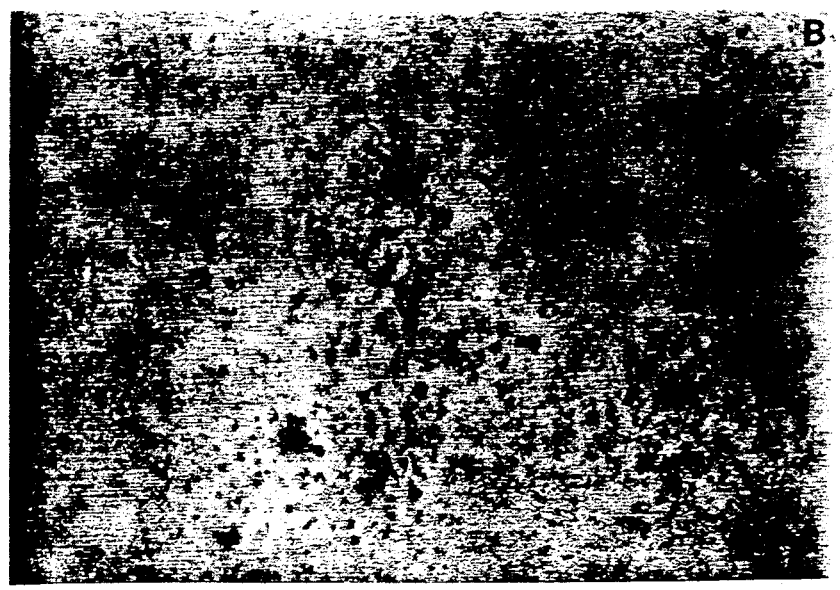
Figure 3C:
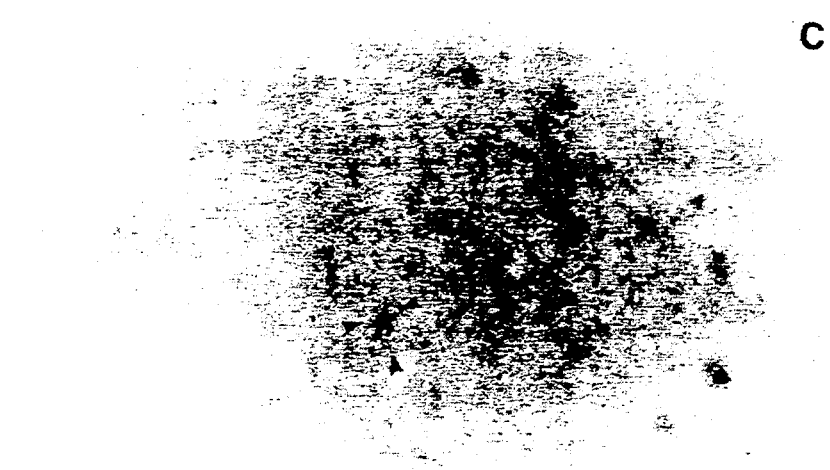
Figure 4A:
FIG. 4A is a high magnification (200×) view of the persisting normal myeloid colony indicated by arrows in FIG. 3C.
Figure 4B:
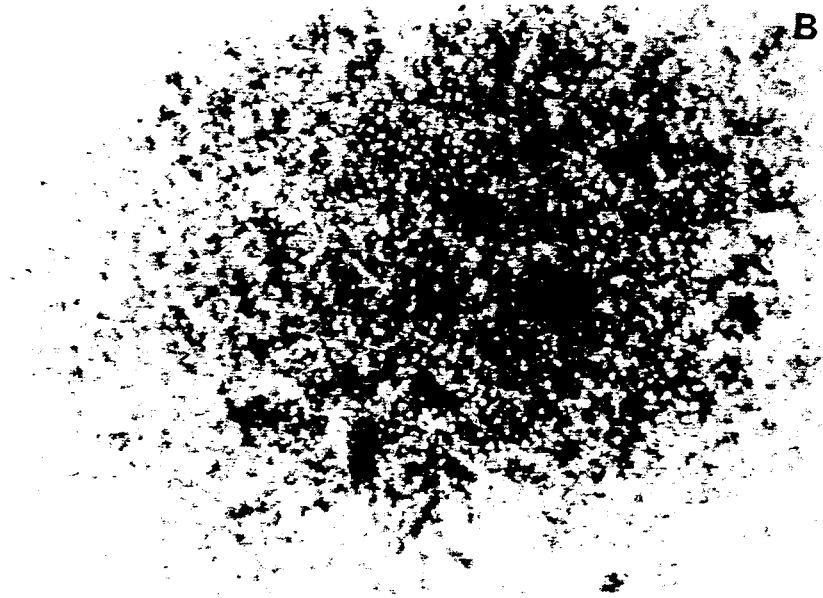
FIG. 4B is a 200× view of the plasma cell leukemia cells shown is FIG. 3A.

FIG. 3 is a series of low magnification (40$\times$) photographs of a 1:1 mixture of ARH-77 cells and normal hematopoietic progenitor cells exposed to: (A) high dose c-myb sense 5'-GCC CGA AGA CCC CGG CAC-3' (40 $\mu$g/ml, t=0; 20 $\mu$g/ml supplement at t=18 hours); (B) low dose c-myb antisense 5'-GTG CCG GGG TCT TCG GGC-3'; (10 $\mu$g/ml t=0; 5 $\mu$g/ml supplement at t=18 hours); and (C) high dose c-myb antisense (40 $\mu$g/ml, t=0; 20 $\mu$g/ml supplement at t=18 hours). The FIG. 3 photographs were taken at t=day 7. While the sense-treated plate (FIG. 3A) was overwhelmed with tumor cells on day 7, the low dose antisense plate (FIG. 3B) displayed persistent, but dramatically reduced numbers of tumor cells. The high dose antisense plate (FIG. 3C) contained a normal myeloid colony with complete disappearance of tumor cells. The arrow heads in FIG. 3C surround a normal myeloid colony which is shown at high magnification in FIG. 4A. A high magnification view of the sense-treated plasma cell leukemia cells of FIG. 3A is shown in FIG. 4B.

EXAMPLE 4

Differential Sensitivity of Tumor (HL-60) and Normal Progenitor Cells Toward c-myb Oligonucleotide The sense/antisense dosing procedure of Example 3 was repeated substituting HL-60 leukemia cells for ARH-77 cells, and utilizing the same dosages and dose times from Example 3. The results are shown in FIGS. 5 and 6.

Figure 5A:
FIG. 5 is a series of microscopic (40×) photographs of a 1:1 mixture of HL-60 cells and normal hematopoietic progenitor cells exposed to 40 µg/ml (t=0) plus 20 µg/ml (t=18 hours) of the c-myb sense oligodeoxynucleotide 5'-GCC CGA AGA CCC CGG CAC-3'(FIG. 5A); 10 µg/ml (t=0) plus 5 µg/ml (t=18 hours) of the c-myb antisense oligodeoxynucleotide 5'-GTG CCG GGG TCT TCG GGC-3'(FIG. 5B); and 40 µg/ml (t=0) plus 20 µg/ml (t=18 hours) of the same c-myb antisense oligomer (FIG. 5C). The photographs were taken at t=day 7.
Figure 5B:
Figure 5C:

FIG. 5 is a series of low (40$\times$) magnification views of a 1:1 mix of HL-60 cells and normal hematopoietic progenitor cells exposed to: (A) high dose c-myb sense, (B) low dose c-myb antisense, and (C) high does c-myb antisense. While a very large HL-60 tumor aggregate appeared in the sample treated with a high dose of c-myb sense oligodeoxynucleotide (FIG. 5A), the colony treated with a low dose of antisense oligonucleotide is much smaller, with fewer tumor cells being apparent (FIG. 5B). A high power view of FIG. 5A is shown in FIG. 6B. At the high dose of antisense (FIG. 5C), normal hematopoietic progenitor cells are unaffected as evidence by the normal myeloid colony indicated by the small arrow head in FIG. 5C. An HL-60 colony was observed to be degenerating, as indicated by the large arrowhead.

Figure 6A:
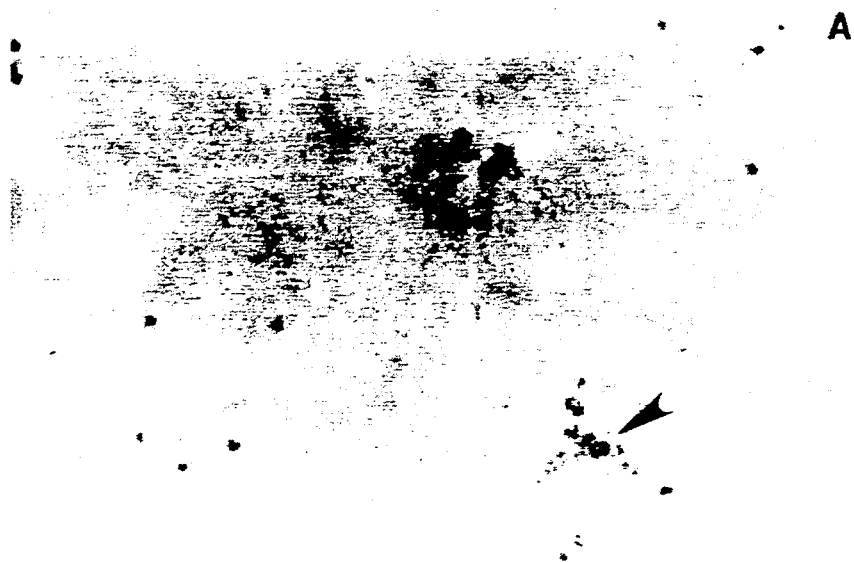
FIG. 6A is a high magnification (200×) view of the persisting normal myeloid colony (small arrow) and degenerating HL-60 colony (large arrow) indicated by the same size arrows in the corresponding lower power view of FIG. 5C.
Figure 6B:
FIG. 6B is a 200× view of the HL-60 cells shown in FIG. 5A.

The colonies featured in FIG. 5C are shown at higher magnification in FIG. 6A.

EXAMPLE 5

Differential Sensitivity of Leukemic T Cells and Normal Progenitor Cells Toward c-myb Oligonucleotide The following experiment further demonstrates that when normal marrow hematopoietic cells are combined with leukemic blast cells in the presence of c-myb antisense oligonucleotide, leukemic cell cloning efficiency is preferentially inhibited, and is accompanied by leukemic cell death. Colony formation in semi-solid cultures was employed as an indicator system to assess survival of clonogenic progenitor cells. Of great importance, many normal hematopoietic progenitor cells were observed to survive exposure to c-myb antisense oligonucleotide, and to continue to form colonies in semi-solid culture medium.

Bone marrow cells from normal consenting donors and cells of the human T cell leukemia cell line CCRF-CEM, obtained from the American Type Culture Collection, were treated as follows. Normal hematopoietic progenitor cells were enriched from light density bone marrow mononuclear cells. The normal cells and the T leukemia cells were placed in liquid suspension cultures (RPMI 1640 with 20% fetal bovine serum, either alone or in a 1:1 mix). Control cultures were left untreated. Treated cultures received varying amounts of the same c-myb sense and antisense oligomers applied in the procedure of Example 3, namely 5–80 µg/ml (~1 µM to 14 µM) at t=0, supplemented with additional oligomer (25% of the initial dose)) at about 18 hours after the start of incubation. Cultures were incubated (5% $CO_2$, 37° C.) for four days, during which time daily cell counts were performed and cell viability was recorded. At the end of the four days, the cells remaining in suspension (to a maximum of $2 \times 10^5$/ml) were transferred to methylcellulose cultures, Leary et al., Blood 71, 1759 (1988) containing 24 U/ml and 5 ng/ml respectively of recombinant human interleukin-3 (rH IL-3) and recombinant human granulocyte macrophage colony stimulating factor (rH GM-CSF). After a total of ten to twelve days in culture, the culture plates were scanned in their entireties with the aid of an inverted microscope, and total colonies per cluster in the dishes were enumerated. To verify the origin of the colonies, that is, whether they were derived from the leukemic or from normal hematopoietic progenitor cells, all cells were removed from the dishes by diluting the methylcellulose in tissue culture medium, transferring the culture dish's contents to a polypropylene tube, and then preparing cytocentrifuge preparations from the contents of the tube for histochemical or immunochemical identification of tumor cells. Histochemical identification of tumor cells was carried out by air drying the cytocentrifugation slides, flooding the slides with Modified Wright's stain (Sigma Chemical Company, #WS 1b) for 5 minutes, followed by rinsing with de-ionized water for 2 minutes. The slides were then coverslipped. Clots were fixed with 4% glutaraldehyde for 8 minutes, flushed with distilled water for 12 minutes, and then dried into a film. The plates were then flooded with Modified Wright's stain for 3 minutes, rinsed in de-ionized water for 6 minutes, and coverslipped. The immunochemical identification of tumor cells was according to the procedure of Gewirtz et al., J. Immunol. 139, 2195 (1987), utilizing the Leu-3a monoclonal antibody (Becton-Dickenson, Mountainview, Calif.). The Leu-3a antibody is directed against the CD4 epitope.

The effect of maintaining the T cell leukemia line and the marrow cells in suspension culture according to the procedure of Example 5, in the presence or absence of the c-myb oligomers, is shown in FIG. 8. In the absence of the oligomers, the T cell leukemia continued to divide in culture, whereas the numbers of bone marrow cells remained essentially unchanged. See FIG. 8A. Cell viability remained high among both cell populations and always exceeded 90%, as assessed by trypan blue exclusion. Treatment of cells with high doses (40 µg/ml, t=0; 10 µg/ml, t=18 hours) of the c-myb sense oligomer did not significantly effect the growth or viability of either cell type (FIG. 8A). In distinct contrast (FIG. 8B), when the T leukemia cells were incubated in suspension with c-myb TM 30 antisense oligomer (20 µg/ml, t=0; 5 µg/ml, t=18 hours) cell proliferation was not only inhibited, but there was a daily decline in cell numbers and viability as well. After four days only approximately 25–30% of the cells initially added to the culture remained; the viability of these cells was also greatly reduced (~70% reduction). The effect of the antisense oligomer is even more dramatic if one compares cell numbers (mean ±standard deviation (hereinafter "SD"); n=4) in the control cultures at four days ($285\pm17 \times 10^4$/ml) with the number remaining in the antisensecontaining culture ($4.7\pm0.8 \times 10^4$/ml). Importantly, when suspended in the same dose of antisense oligomer, the normal marrow mononuclear cells exhibited only a slight decline in numbers and viability over the same time period (~90% of initial cells remaining; viability >90%). These numbers were not significantly altered if hematopoietic growth factors were added to the bone marrow cell suspension during the four day incubation period.

Results from a typical experiment, repeated three times are shown in Table ("BMC" normal bone marrow cells; "MYB S"=c-myb sense oligonucleotide; "MYB AS"=c-myb antisense oligonucleotide; "TNTC" to numerous to count):

TABLE 1

| Cells Plated | No. Cells Added | Oligonucleotide Amt. Added (µg/ml at t = 0; t = 18 hours) | Colony/Cluster Count (Mean ± Standard Deviation) |
|---|---|---|---|
| BMC | 5 × 10⁴/ml | None | 24 ± 4 |
| | | MYB S (20; 5.0) | 31 ± 4 |
| | | MYB S (20; 5.0) | 30 ± 6 |
| T LEUKEMIA | 5 × 10⁴/ml | None | TNTC |
| | | MYB S (20; 5.0) | TNTC |
| | | MYB S (20; 5.0) | 1:1 |
| BMC + LEUKEMIA | 5 × 10⁴/ml of each | None | TNTC |
| | | MYB S (20; 5.0) | TNTC |
| | | MYB AS (2; 0.5) | TNTC |
| | | MYB AS (5; 1.0) | TNTC |
| | | MYB AS (10; 2.5) | 41 ± 5 |

TABLE 1-continued

| Cells Plated | No. Cells Added | Oligonucleotide Amt. Added ($\mu$g/ml at t = 0; t = 18 hours) | Colony/Cluster Count (Mean ± Standard Deviation) |
|---|---|---|---|
| | | MYB AS (20; 5.0) | 34 ± 1 |

Figures 9A, 9B, 9C:
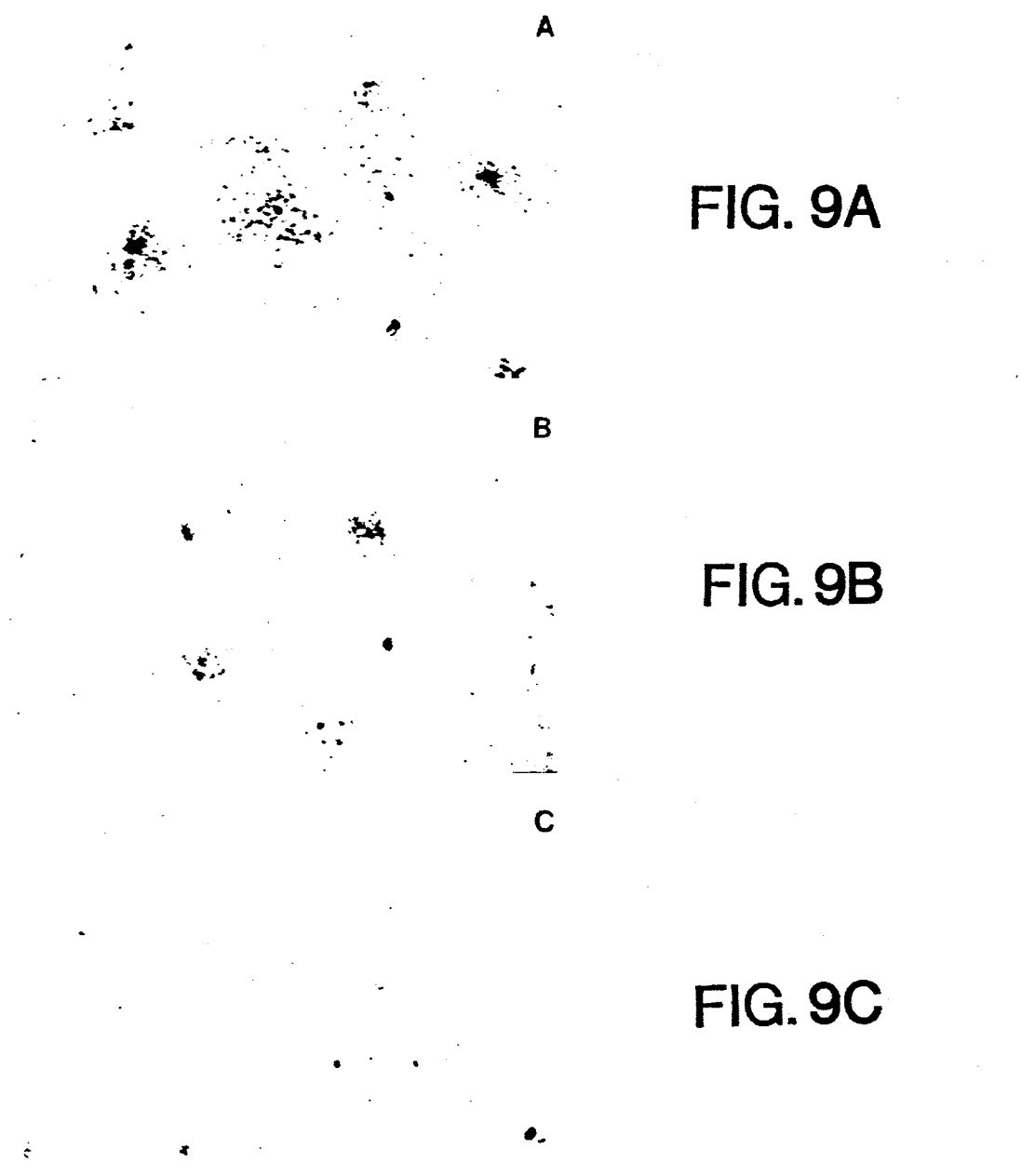

In dishes containing untreated bone marrow cells, colony numbers varied directly with the number of cells plated ($5 \times 10^4$/ml to $2 \times 10^5$/ml), and ranged between 31:4 (mean ±SD) and 274±18. In dishes containing the untreated leukemia cells, cloned at equivalent concentrations, growth was always luxuriant and the numbers of colonies were too numerous to count (TNTC) (FIG. 9A). Exposure to the c-myb sense oligomer had no effect on either normal, or leukemic cell (FIG. 9B) growth when compared to growth in untreated cultures. Colony formation by cells in FIG. 9A and FIG. 9B were essentially identical. When leukemic blasts were cultured alone in the higher doses of antisense oligomer, the numbers of resulting colony/clusters were reduced from TNTC to a maximum of about 2 per $5 \times 10^4$ leukemia cells plated (FIG. 9C). In distinct contrast, in dishes containing bone marrow cells exposed to c-myb antisense, colony formation was not significantly perturbed by the dose and exposure schedule employed (see Table 1). Not unexpectedly then, when bone marrow cells were mixed 1:1 with T leukemia cells and then exposed to the c-myb antisense oligomer at concentrations $\leq 5$ $\mu$g/ml and 1 $\mu$g/ml (t=0 and t=18 hours, respectively), the leukemic cells continued to grow vigorously, and the number of colonies were too numerous to count. However, when the oligomer exposure intensified, a definite dose-response relationship became apparent. At an initial dose of 10 $\mu$g/ml, followed by 2.5 $\mu$g/ml eighteen hours later, the leukemia cells no longer overgrew the plate, and distinct colones could be enumerated in the mixed cell cultures. Nevertheless, histochemical and immunochemical staining demonstrated that ~50% of the colonies that formed in these mixed cell dishes appeared to be of leukemic blast cell origin. When the dose of antisense oligomer employed equaled or exceeded 20 $\mu$g/ml (t=0) followed by 5 $\mu$g/ml (t=18 hours), leukemic colonies could no longer be identified with certainty in the cultures by simple visual analysis.

To more rigorously examine the cultures for residual leukemic elements, the methylcellulose cultures were liquified with tissue culture medium, and the entire cell contents were deposited onto slides by cytocentrifugation. Low (100×) and high (400×) magnification photomicrographs of Wright's stained T leukemia cells after twelve days of culture in methylcellulose are shown in FIGS. 10A and 10B, respectively. Most cells were small, had only a thin rim of cytoplasm, and resembled unactivated lymphocytes, though occasional large, undifferentiated blast cells with prominent nucleoli were also noted (arrows). Neither of these cell types could be identified in the culture dishes containing the leukemia plus normal cell populations which had been cultured in the high dose of c-myb antisense oligomer. As demonstrated in FIGS. 10C (100×) and 10D (400×), respectively, only normally maturing cells could be identified in these cultures. The colonies which developed in the high dose antisense plates were also numerically equivalent to those enumerated in the bone marrow cell control plates.

Immunochemical staining with Leu 3a antibody of either T leukemia cells alone, marrow mononuclear cells alone, or mixtures of normal marrow mononuclear cells and T leukemia cells, maintained in liquid suspension cultures for eight days, corroborated these results. After eight days in culture, only 4% of bone marrow cells stained Leu 3a positive, while ~93% of T cell leukemia cells were labeled with this antibody. When bone marrow cells and T leukemia cells were mixed 1:1, and then stained after eight days in culture, ~98% of cells were stained with Leu 3a in myb sense oligomer. These results indicated that the T leukemia cells outgrew the bone marrow cells, and essentially replaced them in these cultures. In marked contrast, in the mixed cell culture containing the c-myb antisense oligomer, only 3% of the cells stained with Leu 3a after eight days. This value is identical to that obtained in the bone marrow control culture, and suggests again that the leukemic cells were eliminated from the culture.

EXAMPLE 6

Effect of High Dose c-myb Antisense Oligomer On Leukemic Blast Cells From Acute Myelogenous Leukemia Patients The following experiment illustrates the effect of high dose c-myb antisense oligomer exposure on colony/cluster formation by leukemic blast cells isolated directly from patients with acute myelogenous leukemia.

The peripheral blood of leukemic blast cells were isolated form patients with acute myelogenous leukemia by Ficoll gradient centrifugation. The blast cells ($2 \times 10^5$/ml) were washed in fresh tissue culture medium and then exposed to c-myb sense or antisense oligomers (40 $\mu$g/ml, t=0; 10 $\mu$g/ml, t=18 hours) in suspension culture. Four to six hours after addition of the last dose of oligomer, the blast cells were seeded into plasma clot or methylcellulose cultures and cultured for ten to twelve days to assess the presence of residual colony/cluster forming units. Cell colonies and cell clusters were enumerated in sense (S) and antisense (AS) containing plates, and the values compared to growth in control cultures which contained no oligomers. The results are expressed in Table 2 as % residual control culture growth (arbitrary 100% value). Significance of changes in colony/cluster growth in AS-treated plates, in comparison to that observed in controls, is given as a P value derived by Student's t test for unpaired samples.

TABLE 2

| Case # | Cell Colonies S/AS[1] | Cell Clusters S/AS | P Value Colony/Cluster |
|---|---|---|---|
| #1 | 86%/18% | 60%/37% | [.058]/[.080] |
| #4 | NG[2] | 90%/28% | [—]/[.036] |
| #5 | NG | 70%/22% | [—]/[.101] |
| #6 | NG | 79%/22% | [—]/[.026] |
| #7 | 170%/100% | 76%/128% | [.423]/[.502] |
| #8 | 92%/11% | 96%/46% | [.008]/[.020] |
| #10 | NG | 190%/216% | [—]/[.034] |
| #11 | 45%/14% | 58%/21% | [.021]/[.084] |
| #14 | 68%/01% | 90%/53% | [.152]/[.071] |
| #15 | 66%/81% | 100%/100% | [.736]/[.896] |
| #16 | NG | 66%/24% | [—]/[.001] |
| #17 | NG | 16%/8% | [—]/[.023] |
| #18 | NG | 110%/77% | [—]/[.164] |
| #19 | 113%/116% | 91%/91% | [.717]/[.763] |
| #20 | 92%/09% | 100%/50% | [.051]/[.009] |
| #21 | 94%/00% | 90%/06% | [.006]/[.004] |
| #22 | 80%/13% | 103%/11% | [.001]/[.015] |
| #23 | 63%/06% | 74%/27% | [.001]/[.004] |

TABLE 2-continued

| Case # | Cell Colonies S/AS[1] | Cell Clusters S/AS | P Value Colony/Cluster |
|---|---|---|---|
| #24 | 87%/17% | 91%/26% | [.002]/[.018] |
| #25 | 100%/00% | 107%/38% | [.019]/[.364] |
| #26 | 76%/00% | 89%/00% | [.009]/[.001] |
| #27 | 79%/21% | 59%/18% | [.014]/[.043] |
| #28 | 88%/20% | 94%/152% | [.009]/[.096] |

[1]S/AS = percentage of cell colonies or cell clusters remaining in sense (S) or antisense (AS) containing plates, compared to growth in control cultures which contained no oligomers.
[2]NG = no growth.

Of the twenty-eight cases studied, we were able to gather colony, and/or cluster formation data in twenty-three cases (Table 2). Growth of cells from patients #2, #3, #9 and #12-#13 was too poor to evaluate the effect of treatment. A decline in either colony or cluster formation in comparison to growth in untreated cultures was observed in eighteen of the twenty-three evaluable cases (78%). Of those cases in which this response was observed, the decline in colony number was statistically significant ($p \leq 0.05$) in 11/13 cases (85%). In the two cases where the decrease was not of statistical significance, the p values were 0.058 (Case #1) and 0.051 (Case #20). Similarly, the decrement in cluster formation was statistically significant in 13/17 (76%) of the cases. The degree of inhibition was also impressive. Mean ($\pm$SD) residual leukemic colony formation in the eleven responding cases was $10.0 \pm 7.9\%$ of control (untreated leukemia cell) colony formation. Mean ($\pm$SD) residual leukemic cluster formation in the seventeen responding cases was $25.7 \pm 15.3\%$ of control.

EXAMPLE 7

Complete Purging of Patient-Derived Myeloid Leukemia Cells From Normal Bone Marrow Cells The following experiment demonstrates that a more intensive exposure to the antisense c-myb oligomer results in complete elimination of myeloid leukemic progenitor cells from a mixture of normal bone marrow progenitor cells, with adequate survival of the normal progenitor cells.

Normal bone marrow cells and blasts obtained from Case #26 (Example 6, Table 2) were utilized for purging using the T cell purging protocol described in Example 5. The only modification involved was the addition of oligomer (20 μg/ml) just prior to plating after four days in suspension culture. In untreated cultures, the blasts formed $5.5 \pm 3.5$ (mean $\pm$SD per $2 \times 10^5$ cells plated) colonies and $157 \pm 8.5$ clusters in growth factor stimulated cultures. The addition of c-myb sense oligomers at doses equivalent to those added to antisense containing cultures did not significantly alter these numbers ($19.5 \pm 7$ colonies and $40.5 \pm 7.8$ clusters). As expected (see Table 2), antisense oligomers again totally inhibited colony/cluster formation by the leukemic blasts. Colony formation as also inhibited in the plates containing normal bone marrow cells, but only by ~50% in comparison to untreated control plates. (Control colony formation = $296 \pm 40$ per $2 \times 10^5$ cells plated; Treated $149 \pm 15.5$ per $2 \times 10^5$ cells). Histochemical staining of the leukemic blast cell cultures revealed only scattered residual cells in the antisense treated plates (FIG. 11A: 100×). At high magnification, these "cells" appeared to be non-viable naked nuclei (FIG. 11B: 400×). As was stated above, at an equivalent antisense oligomer dose, bone marrow cells formed numerous, though smaller, colonies which contained cells that had matured normally (FIG. 11C and 11D; 100× and 400×, respectively). In the culture dishes in which normal marrow and leukemic blast cells had been mixed in a 1:1 ratio, only normal elements could be identified with certainty (FIG. 11E: 100×; FIG. 11F: 400×). Stars in FIG. 11F mark mature myeloid elements (polymorphonuclear leukocytes, bands, and metamyelocytes).

C-myb oligonucleotide, administered to cell cultures at concentrations utilized above, effectively kills neoplastic cells. The same concentrations, however, are non-toxic to normal progenitor cells. Thus, the oligomers are useful as anti-neoplastic agents, particularly as bone marrow purging agents.

The following non-limiting example illustrates one methodology for bone marrow purging according to the present invention.

EXAMPLE 8

Bone Marrow Purging with c-myb Antisense Oligonucleotide

Bone marrow is harvested from the iliac bones of a donor under general anesthesia in an operating room using standard techniques. Multiple aspirations are taken into heparinized syringes. Sufficient marrow is withdrawn so that the marrow recipient will be able to receive about $4 \times 10^8$ to about $8 \times 10$hu 8 processed marrow cells per kg of body weight. Thus, about 750 to 1000 ml of marrow is withdrawn. The aspirated marrow is transferred immediately into a transport medium (TC-199, Gibco, Grand Island, New York) containing 10,000 units of preservative-free heparin per 100 ml of medium. The aspirated marrow is filtered through three progressively finer meshes until a single cell suspension results, i.e., a suspension devoid of cellular aggregates, debris and bone particles. The filtered marrow is then processed further into an automated cell separator (e.g., Cobe 2991 Cell Processor) which prepares a "buffy coat" product, (i.e., leukocytes devoid of red cells and platelets). The buffy coat preparation is then placed in a transfer pack for further processing and storage. It may be stored until purging in liquid nitrogen using standard procedures. Alternatively, purging can be carried out immediately, then the purged marrow may be stored frozen in liquid nitrogen until it is ready for transplantation.

The purging procedure may be carried out as follows: Cells in the buffy coat preparation are adjusted to a cell concentration of about $2 \times 10^7$/ml in TC-199 containing about 20% autologous plasma. C-myb antisense oligodeoxynucleotide, for example, in a concentration of about 8 mg/ml is added to the transfer packs containing the cell suspension. Recombinant human hematopoietic growth factors, e.g., rH IL-3 or rH GM-CSF, may be added to the suspension to stimulate growth of hematopoietic neoplasms and thereby increase their sensitivity c-myb antisense oligonucleotide toxicity. The transfer packs are then placed in a 37° C. waterbath and incubated for 18-24 hours with gentle shaking. The cells may then either be frozen in liquid nitrogen or washed once at 4° C. in TC-199 containing about 20% autologous plasma to remove unincorporated oligomer. Washed cells are then infused into the recipient. Care must be taken to work under sterile conditions wherever possible and to maintain scrupulous aseptic techniques at all times.

EXAMPLE 9

Inhibition of Leukemic T Cells and Tumor (HL-60) Cells by c-myb Antisense Oligonucleotide The following experiment is directed to the inhibition of growth of malignant hematopoietic cells with further c-myb antisense oligonucleotides.

Four 18-mers, designated oligomers A through D, were prepared:

(A) 5'-GCC ATG GCC CGA AGA CCC-3', the sense oligomer corresponding to c-myb nucleotides 111 through 129;

(B) 5'-GGG TCT TCG GGC CAT GGC-3', the antisense oligomer to c-myb nucleotides 111 through 129;

(C) 5'-CGC GTA CCG CAG GAA CCC-3', a "scrambled" version of 18-mer (A); and (D) 5'-ACT GCT ATA TAT GCT GTG-3', the antisense oligomer to c-myb nucleotides 129 through 147.

CCRF-CEM cells ($1 \times 10^5$ cells) were seeded into 500 $\mu$l of tissue culture medium containing 0-80 $\mu$g/ml of oligomer A, B, C or D (t=0). The cultures were supplemented with additional oligomer (25% of the initial dose at t=18 hours). A control culture received no oligomer. Cultures were incubated for four days, after which time a cell count was taken. The results, as a function of oligonucleotide dosage, are set forth in Table 3:

TABLE 3

| Oligomer Dosage at t = 0/t = 18 hrs. (ug/ml) | CELL COUNT (Cells/$\mu$l; Mean $\pm$ Standard Deviation) | | | |
|---|---|---|---|---|
| | Oligomer A | Oligomer B | Oligomer C | Oligomer D |
| Control (no oligomer) | 968 $\pm$ 17 | 1636 $\pm$ 39 | 1814 $\pm$ 58 | 1616 $\pm$ 38 |
| 10/2.5 | 1279 $\pm$ 15 | 996 $\pm$ 13 | 1452 $\pm$ 18 | 1146 $\pm$ 16 |
| 20/5 | 1297 $\pm$ 39 | 646 $\pm$ 12 | 1367 $\pm$ 36 | 810 $\pm$ 15 |
| 40/10 | 1202 $\pm$ 29 | 616 $\pm$ 17 | 1290 $\pm$ 28 | 723 $\pm$ 37 |
| 80/20 | 1136 $\pm$ 34 | 504 $\pm$ 22 | 1317 $\pm$ 35 | 690 $\pm$ 9 |

Neither the sense (oligomer A) or "scrambled" sense (oligomer C) molecules significantly effected leukemic cell growth. Both authentic antisense oligomers (B, D) gave inhibition. Oligomer B (70% inhibition), directed to c-myb transcript nucleotides 111-129, was more potent than oligomer D (57% inhibition), which is directed to c-myb transcript nucleotides 129-147. This result indicates that the most efficient inhibition of translation is obtained by inhibiting translation via hybridization of antisense oligomers at or near the site of translation initiation (nucleotides 114-116).

Very similar results were obtained with HL-60 cells using oligomers A, B and C. However oligomer D inhibited cell growth only ~25%, again indicating that the most efficient inhibition of translation is obtained at or near the site of translation inhibition.

The present invention may be embodied in other specific forms without departing from the spirit or essential attributes thereof and, accordingly, reference should be made to the appended claims, rather than to the foregoing specification, as indicating the scope of the invention.

We claim:

1. A pharmaceutical composition comprising a pharmaceutical carrier and an oligonucleotide which has a nucleotide sequence complementary to at least a portion of the mRNA transcript of the human c-myb gene, said oligonucleotide being hybridizable to said mRNA transcript.

2. A composition according to claim 1 wherein the oligonucleotide comprises an at least 15-mer oligodeoxynucleotide.

3. A composition according to claim 2 wherein the oligodeoxynucleotide has a deoxynucleotide sequence complementary to a portion of the c-myb mRNA transcript including the translation initiation codon of said transcript.

4. A composition according to claim 2 wherein the oligodeoxynucleotide has a deoxynucleotide sequence complementary to a portion of the c-myb mRNA transcript beginning with the codon immediately downstream from the translation initiation codon of said transcript.

5. A composition according to claim 2 wherein the oligodeoxynucleotide has a deoxynucleotide sequence complementary to a portion of the c-myb mRNA transcript which includes at least a portion of the 5'-untranslated region of said transcript.

6. A composition according to claim 2 wherein the oligodeoxynucleotide comprises from a 15-mer to a 21-mer.

7. A composition according to claim 4 wherein the oligodeoxynucleotide is selected from the group of oligodeoxynucleotides consisting of:

5'-GCT GTG CCG GGG TCT TCG GGC-3',

5'-CT GTG CCG GGG TCT TCG GGC-3',

5'-T GTG CCG GGG TCT TCG GGC-3',

5'-GTG CCG GGG TCT TCG GGC-3',

5'-TG CCG GGG TCT TCG GGC-3',

5'-G CCG GGG TCT TCG GGC-3' and

5'-CCG GGG TCT TCG GGC-3'.

8. A composition according to claim 7 wherein the oligodeoxynucleotide comprises 5'-GTG CCG GGG TCT TCG GGC-3'.

9. A composition according to claim 5 wherein the oligodeoxynucleotide is selected from the group of oligodeoxynucleotides consisting of:

5'-CCG GGG TCT TCG GGC CAT GGC-3',

5'-CG GGG TCT TCG GGC CAT GGC-3',

5'-G GGG TCT TCG GGC CAT GGC-3',

5'-GGG TCT TCG GGC CAT GGC-3',

5'-GG TCT TCG GGC CAT GGC-3',

5'-G TCT TCG GGC CAT GGC-3' and

5'-TCT TCG GGC CAT GGC-3'.

10. A composition according to claim 9 wherein the oligodeoxynucleotide comprises 5'-GGG TCT TCG GGC CAT GGC 3'.

11. A method for treating in vivo or ex vivo hematologic neoplasms characterized by c-myb expression comprising administering to a host in need of such treatment or to cells harvested from such host an effective amount of an oligonucleotide which has a nucleotide sequence complementary to at least a portion of the mRNA transcript of the human c-myb gene, said oligonucleotide being hybridizable to said mRNA transcript.

12. The method according to claim 11 wherein the oligonucleotide is an at least 15-mer oligodeoxynucleotide.

13. A method according to claim 12 wherein the oligodeoxynucleotide has a deoxynucleotide sequence complementary to a portion of the c-myb mRNA transcript including the translation initiation codon of said transcript.

14. A method according to claim 12 wherein the oligodeoxynucleotide has a deoxynucleotide sequence complementary to a portion of the c-myb mRNA transcript beginning with the codon immediately downstream from the translation initiation codon of said transcript.

15. A method according to claim 12 wherein the oligodeoxynucleotide has a deoxynucleotide sequence complementary to a portion of the c-myb mRNA transcript which includes at least a portion of the 5'-untranslated region of said transcript.

16. A method according to claim 12 wherein the oligodeoxynucleotide comprises from a 15-mer to a 21-mer.

17. A method according to claim 14 wherein the oligodeoxynucleotide is selected from the group consisting of:

5'-GCT GTG CCG GGG TCT TCG GGC-3',

5'-CT GTG CCG GGG TCT TCG GGC-3',

5'-T GTG CCG GGG TCT TCG GGC-3',

5'-GTG CCG GGG TCT TCG GGC-3',

5'-TG CCG GGG TCT TCG GGC-3',

5'-G CCG GGG TCT TCG GGC-3' and

5'-CCG GGG TCT TCG GGC-3'.

18. A method according to claim 17 wherein the oligodeoxynucleotide comprises 5'-GTG CCG GGG TCT TCG GGC-3'.

19. A method according to claim 15 wherein the oligodeoxynucleotide is selected from the group of oligodeoxynucleotides consisting of:

5'-CCG GGG TCT TCG GGC CAT GGC-3',

5'-CG GGG TCT TCG GGC CAT GGC-3',

5'-G GGG TCT TCG GGC CAT GGC-3',

5'-GGG TCT TCG GGC CAT GGC-3',

5'-GG TCT TCG GGC CAT GGC-3',

5'-G TCT TCG GGC CAT GGC-3' and

5'-TCT TCG GGC CAT GGC-3'.

20. A method according to claim 19 wherein the oligodeoxynucleotide comprises 5'-GGG TCT TCG GGC CAT GGG-b 3'.

21. A method according to any of claims 11, 12, 13, 14, 15, 16, 17, 18, 19 or 20 comprising treating aspirated bone marrow cells.

22. A method according to claim 11 wherein the hematologic neoplasm comprises acute myeloid leukemia.

23. A method according to claim 11 wherein the hematologic neoplasm comprises chronic myeloid leukemia.

24. A method according to claim 11 wherein the hematologic neoplasm comprises acute lymphatic leukemia.

25. A method according to claim 11 wherein the hematologic neoplasm comprises chronic lymphatic leukemia.

26. A method according to claim 11 wherein the hematologic neoplasm comprises a non-Hodgkin's lymphoma.

27. A method for inducing suppression of lymphocyte proliferation comprising administering to a host in need thereof an effective amount of an oligonucleotide which has a nucleotide sequence complementary to at least a portion of the mRNA transcript of the human c-myb gene, said oligonucleotide being hybridizable to said mRNA transcript.

28. A method according to claim 27 wherein the oligonucleotide is an at least 15-mer oligodeoxynucleotide.

29. A method according to claim 28 wherein the oligodeoxynucleotide has a deoxynucleotide sequence complementary to a portion of the c-myb mRNA transcript including the translation initiation codon of said transcript.

30. A method according to claim 28 wherein the oligodeoxynucleotide has a deoxynucleotide sequence complementary to a portion of the c-myb mRNA transcript beginning with the codon immediately downstream from the translation initiation codon of said transcript.

31. A method according to claim 28 wherein the oligodeoxynucleotide has a deoxynucleotide sequence complementary to a portion of the c-myb mRNA transcript which includes at least a portion of the 5'-untranslated region of said transcript.

32. A method according to claim 28 wherein the oligodeoxynucleotide comprises from a 15-mer to a 21-mer.

33. A method according to claim 30 wherein the oligodeoxynucleotide is selected from the group consisting of:

5'-GCT GTG CCG GGG TCT TCG GGC-3',

5'-CT GTG CCG GGG TCT TCG GGC-3',

5'-T GTG CCG GGG TCT TCG GGC-3',

5'-GTG CCG GGG TCT TCG GGC-3',

5'-TG CCG GGG TCT TCG GGC-3',

5'-G CCG GGG TCT TCG GGC-3' and

5'-CCG GGG TCT TCG GGC-3'.

34. A method according to claim 33 wherein the oligodeoxynucleotide comprises 5'-GTG CCG GGG TCT TCG GGC-3'.

35. An oligonucleotide which has a nucleotide sequence complementary to at least a portion of the mRNA transcript of the human c-myb gene, said oligonucleotide being hybridizable to said mRNA transcript.

36. An oligonucleotide according to claim 35 which comprises at least a 15-mer oligodeoxynucleotide.

37. An oligodeoxynucleotide according to claim 36 which has a deoxynucleotide sequence complementary to a portion of the c-myb mRNA transcript including the translation initiation codon of said transcript.

38. An oligodeoxynucleotide according to claim 36 which has a deoxynucleotide sequence complementary to a portion of the c-myb mRNA transcript beginning with the codon immediately downstream from the translation initiation codon of said transcript.

39. An oligodeoxynucleotide according to claim 36 which has a deoxynucleotide sequence complementary to a portion of the c-myb mRNA transcript which includes at least a portion of the 5'-untranslated region of said transcript.

40. An oligodeoxynucleotide according to claim 36 which comprises from a 15-mer to a 21-mer.

41. An oligodeoxynucleotide according to claim 38 selected from the group consisting of:

5'-GCT GTG CCG GGG TCT TCG GGC-3',

5'-CT GTG CCG GGG TCT TCG GGC-3',

5'-T GTG CCG GGG TCT TCG GGC-3',

5'-GTG CCG GGG TCT TCG GGC-3',

5'-TG CCG GGG TCT TCG GGC-3',

5'-G CCG GGG TCT TCG GGC-3' and

5'-CCG GGG TCT TCG GGC-3'.

42. An oligodeoxynucleotide according to claim 41 wherein the oligodeoxynucleotide comprises 5'-GTG CCG GGG TCT TCG GGC-3'.

43. An oligodeoxynucleotide according to claim 39 selected from the group consisting of:

5'-CCG GGG TCT TCG GGC CAT GGC-3',

5'-CG GGG TCT TCG GGG CAT GGC-3',

5'-G GGG TCT TCG GGC CAT GGC-3',

5'-GGG TCT TCG GGC CAT GGC-3',

5'-GG TCT TCG GGC CAT GGC-3',

5'-G TCT TCG GGC CAT GGC-3' and

5'-TCT TCG GGC CAT GGC-3'.

44. An oligodeoxynucleotide according to claim 43 wherein the oligodeoxynucleotide comprises 5'-GGG TCT TCG GGC CAT GGC-3'.

* * * * *

UNITED STATES PATENT AND TRADEMARK OFFICE
CERTIFICATE OF CORRECTION

PATENT NO. : 5,098,890

DATED : March 24, 1992

INVENTOR(S) : Alan M. Gewirtz and Bruno Calabretta

It is certified that error appears in the above-identified patent and that said Letters Patent is hereby corrected as shown below:

Column 2, line 17, (both occurrences) change "c fos" and "C fos" to --c-fos-- and --C-fos--; column 2, line 32, change "c fos" to --c-fos--; column 6, line 9, change "c-myl" to --c-myb--; column 23, line 50, change the second occurrence of "GGG" to --GGC--; column 23, line 62, change "GGG-b 3'" to --GGC-3'--; column 26, line 15, change the second occurrence of "GGG" to --GGC--.

Signed and Sealed this

Twenty-ninth Day of June, 1993

Attest:

MICHAEL K. KIRK

Attesting Officer

Acting Commissioner of Patents and Trademarks